United States Patent [19]
Le et al.

[11] Patent Number: 6,153,115
[45] Date of Patent: *Nov. 28, 2000

[54] MONITOR OF PLASMA PROCESSES WITH MULTIVARIATE STATISTICAL ANALYSIS OF PLASMA EMISSION SPECTRA

[75] Inventors: Minh Le, Colorado Springs, Colo.; Kuang Han Chen, Boston, Mass.; Taber H. Smith, Dallas, Tex.; Duane S. Boning, Belmont; Herbert H. Sawin, Chestnut Hill, both of Mass.

[73] Assignee: Massachusetts Institute of Technology, Cambridge, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/956,575

[22] Filed: Oct. 23, 1997

[51] Int. Cl.⁷ .................................................. G01J 3/457
[52] U.S. Cl. .................................................. 216/60; 438/9
[58] Field of Search ...................... 156/345; 438/9, 438/16; 216/60, 67, 72; 118/663, 695, 696, 698, 708, 712

[56] References Cited

U.S. PATENT DOCUMENTS

| | | | |
|---|---|---|---|
| 4,491,499 | 1/1985 | Jerde et al. ............................ | 156/626 |
| 5,160,402 | 11/1992 | Cheng .................................... | 156/627 |
| 5,288,367 | 2/1994 | Angell et al. .......................... | 156/626 |
| 5,308,414 | 5/1994 | O'Neill et al. ........................ | 156/626 |
| 5,347,460 | 9/1994 | Gifford et al. ..................... | 364/468.28 |
| 5,374,327 | 12/1994 | Imahashi et al. ..................... | 156/626 |
| 5,405,488 | 4/1995 | Dimitrelis et al. .................... | 156/627 |
| 5,467,883 | 11/1995 | Frye et al. ............................. | 216/60 |
| 5,500,076 | 3/1996 | Jerbic .................................... | 438/9 |
| 5,552,016 | 9/1996 | Ghanayem ......................... | 156/627.1 |
| 5,653,894 | 8/1997 | Ibbotson et al. ....................... | 216/59 |
| 5,654,903 | 8/1997 | Reitman et al. ....................... | 702/81 |
| 5,658,423 | 8/1997 | Angell et al. .......................... | 438/9 |
| 5,711,843 | 1/1998 | Jahns ..................................... | 156/345 |
| 5,871,658 | 2/1999 | Tao et al. .............................. | 216/60 |

FOREIGN PATENT DOCUMENTS

| | | | |
|---|---|---|---|
| 0768701 | 4/1997 | European Pat. Off. | ......... H01J 37/32 |
| 9702593 | 1/1997 | WIPO | ......... H01L 21/3065 |

OTHER PUBLICATIONS

Rangan et al., Modeling and Filtering of Optical Emission Spectroscopy Data for Plasma Etching Systems, Semiconductor Manufacturing Conference Proceedings, 1997.

(List continued on next page.)

Primary Examiner—Randy Gulakowski
Assistant Examiner—Allan Olsen
Attorney, Agent, or Firm—Theresa A. Lober

[57] ABSTRACT

Plasma process analysis techniques are provided. The intensity of each of a number, P, of a plurality of radiation wavelengths that are emitted from a plasma process are monitored as the process proceeds. Indications of P-dimensional correlations between the intensities of the P monitored wavelengths are produced as the process proceeds. Then the produced correlation indications are compared with a prespecified correlation indication generated based on historical conditions for the plasma process, to determine the status condition of the process as the process proceeds. With this technique, the use of a priori, expected, specific templates is not required for evaluating radiation emission data during a plasma process. Instead the techniques investigate and discover the multiple complex correlations that form between various radiation emission wavelengths during a plasma process, and do not impose an expectation for a specific correlation or trend between the various wavelengths. The discovered correlations found to exist between the radiation wavelengths are then employed for monitoring a plasma process based on the discovered correlations. The analysis techniques enables evaluation of interactions occurring across the entire spectrum of detected radiation emission wavelengths, and thus can accomplish detection and analysis of changes in a given plasma process due to shifts in the electrical and physical process environment as well as changes in a given process due to procession through stages of the process.

40 Claims, 25 Drawing Sheets

OTHER PUBLICATIONS

Oshima, "Optical Spectroscopy in Reactive Sputter Etching and Its Application to Process Control," *japaneses Jnl. of Appl. Phys.,* vol. 20, No. 4, pp. 683–690, Apr., 1981.

Russell et al., "Chromatic monitoring for the processing of materials with plasmas," *IEE Pro.–A. Science Measurement & Technology,* vol. 141, No. 2, pp. 99–104, Mar., 1994.

Litvak, "End point control via optical emission spectroscopy," 8257b *Jnl. of Vacuum Science & Technology* B, vol. 14, No. 1, pp. 516–520, Jan./Feb., 1996.

MacGregor et al., "Statistical Process Control of Multivariate Processes," *Control Eng. Practice,* vol. 3, No. 3, pp. 403–414, 1995.

Barna et al., "Sensor Information from a Lam 9600 Metal Etch Process," Proceedings of the Symp. On Process Control, Diagnostics, and Modeling in Semiconductor Manufacturing.

Electrochemical Society, Reno, NV, May 21–26, 1995, Meyyapan et al., Eds., pp. 306–326.

Allen et al., "Application of neural networks to plasma etch end point detection," *Journal of Vacuum Science Technology B,* vol. 14, No. 1, pp. 498–503, Jan./Feb., 1996.

White et al., "Spatial Characterization of Wafer State Using Principal Component Analysis of Optical Emission Spectra in Plasma Etch," *IEEE Trans. on Semiconductor Manufacturing,* vol. 10, No. 1, pp. 52–61, Feb. 1997.

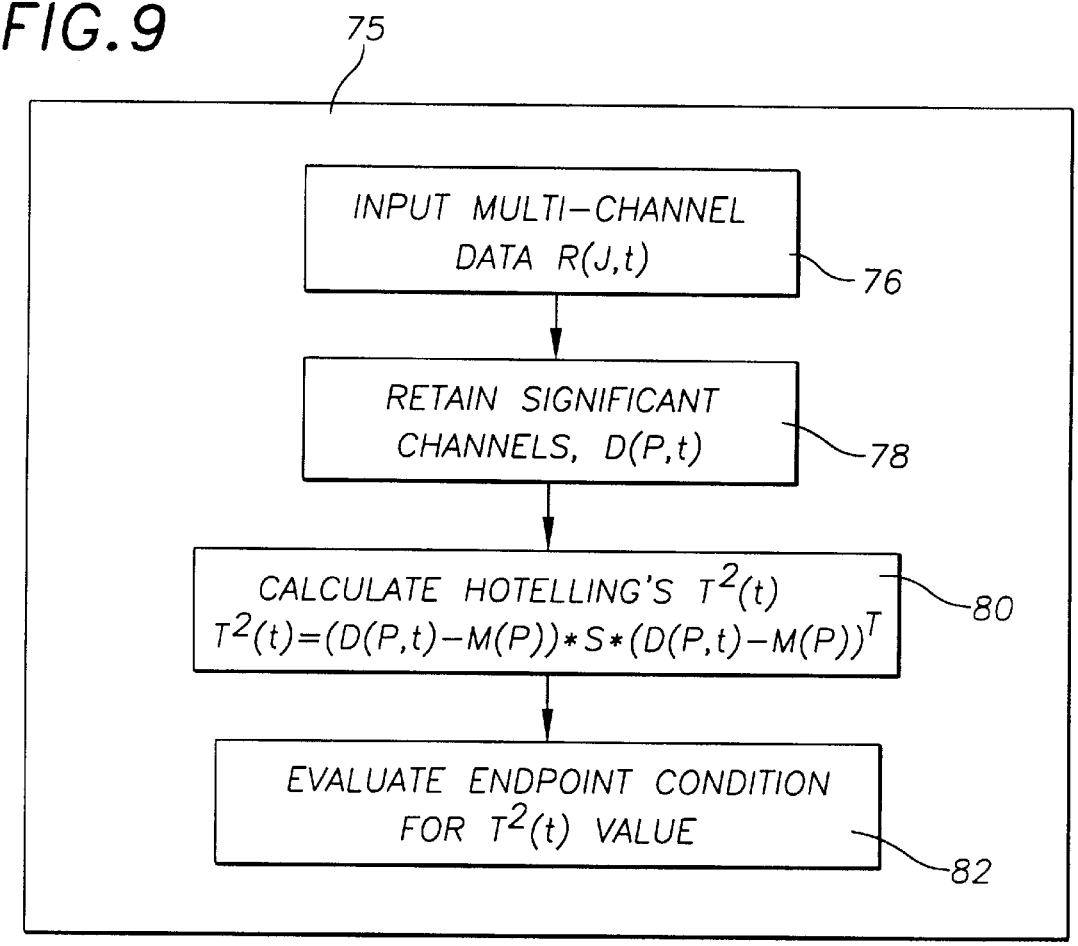
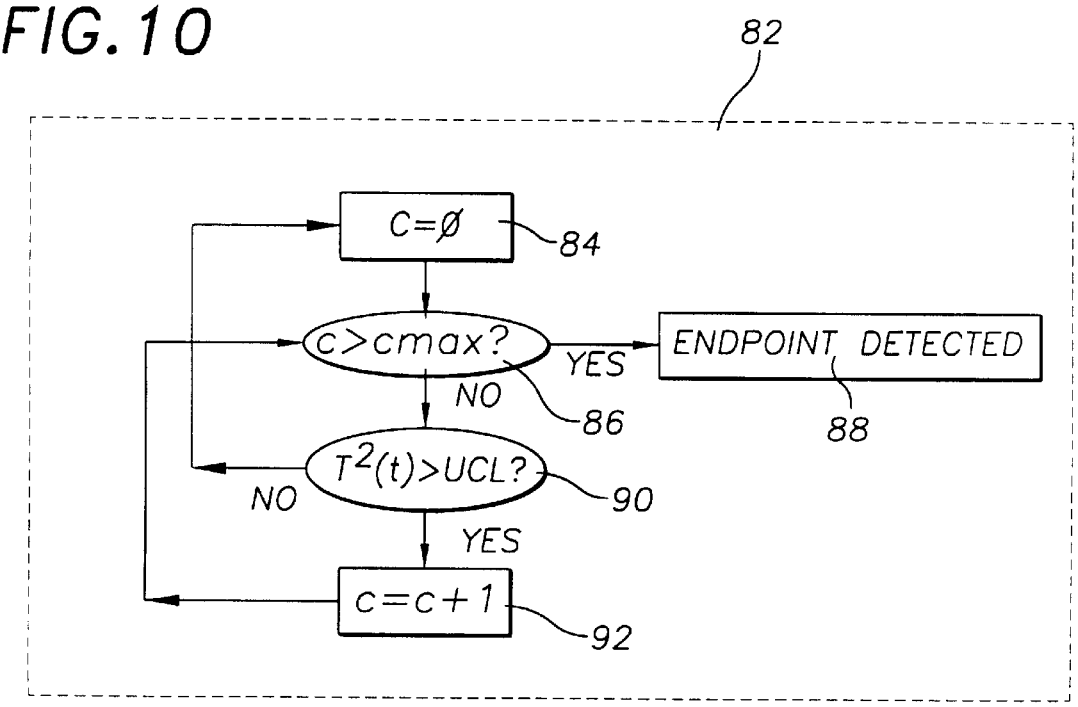

WHERE SUPERSCRIPT $T$ DENOTES THE TRANSPOSE

MONITOR OF PLASMA PROCESSES WITH MULTIVARIATE STATISTICAL ANALYSIS OF PLASMA EMISSION SPECTRA

BACKGROUND OF THE INVENTION

This invention relates to techniques for monitoring plasma processes used in semiconductor circuit fabrication, and more particularly relates to techniques for detection of various stages in such plasma processes.

Plasma processing is a well-established and accepted technology employed in the fabrication of semiconductor circuits. In particular, plasma etching techniques have become standardized processes for patterning semiconductor material layers. A plasma etch process typically involves the reaction of ionized reactant gases in a plasma state with portions of a material layer to be removed from a semiconductor wafer. Typically a patterned masking material is provided over portions of the layer to protect such portions from the reactant plasma gases, whereby the layer can be etched in a specific pattern during exposure to the reactive plasma gases.

A plasma etch process conventionally includes a series of stages such as pre-etch, main etch, and post-etch stages. A pre-etch stage includes, e.g., cleaning of the plasma chamber, striking of a plasma, and stabilization of a plasma; the main etch stage includes the material layer etch process, which may consist of multiple etch processes of differing chemistry; and the post-etch stage includes, e.g., an additional etch known as an over-etch process, and post-etch chamber cleaning. During each stage, the reactant gases introduced and ionized in the plasma chamber, as well as the product gases resulting from plasma reaction with the semiconductor material, interact with each other as well as with electrical and physical processes in a complex and nonlinear manner.

It has been demonstrated that characteristics of this complex plasma interaction are indicated in radiation emissions produced during the plasma process; the gases present in the plasma produce radiative emissions that are characteristic of the atomic and molecular species present in the chamber. Spectral analysis of the radiative emissions produced during an etch process have correspondingly been employed in known techniques for detecting the status of an etch process. A large effort has gone specifically to development of techniques employing optical emission analysis for detecting the main etch stage conclusion, known as the etch endpoint. Plasma etch endpoint is generally considered to be that point in time when the last traces of a layer being etched are removed. Optimally, the main etch stage is stopped just as the etching layer is removed and before underlying layers are damaged. Endpoint detection is thus a critical monitoring capability for successful plasma etching.

Plasma etch endpoint detection has been demonstrated with a range of techniques, the majority of which are based on monitoring of plasma radiation emission intensity at one or more wavelengths characteristic of the gaseous etch reactants and/or etch products associated with a main etch stage. When the monitored intensity changes in a prescribed manner with respect to a prespecified threshold intensity, etch endpoint detection is signaled. Other suggested detection techniques include, e.g., plasma impedance sensing.

When the material layer area being etched is not greatly exposed, i.e., when the etch pattern has a small exposed open area and a large masked area that is protected from the plasma, it is found that measurable changes in the emission intensity characteristic of the etch stage endpoint can be so small that analysis of the emission may not be meaningful. The radiative and electrical noise generated by the system can be so large as to swamp the measurable radiative emission. But as the linewidth of semiconductor devices continues to decrease, credible and reliable plasma etch endpoint detection for low open area etch patterns is critical. Further, as can be expected, the challenge posed by small linewidth devices for credible plasma etch endpoint detection also extends to credible monitoring of the other stages of the plasma etch process. Conventional plasma process monitoring techniques have been found to provide only suboptimal detection and monitoring results at small device linewidths, however.

It is also found that whatever device linewidth is to be etched, the condition of the plasma etch equipment can change over time due to, e.g., build up of deposits in the plasma chamber, so-called seasoning of the chamber, changes to semiconductor materials, and other factors, all of which can cause changes in what is detected as radiative emissions during the etch process. As a result, a satisfactory emission analysis for one etch process may be insufficient for a later etch process carried out under the same process conditions. Specifically, a static analysis prescription that cannot automatically consider changes in the plasma process environment can produce invalid process indications over time. This impediment, typical of conventional plasma process monitoring systems, is further worsened by small linewidth etch scenarios, leading to substantially suboptimal plasma process monitoring and control capabilities.

SUMMARY OF THE INVENTION

The invention overcomes limitations of conventional plasma process monitoring systems by eliminating the use of a priori, expected, specific templates for evaluating radiation emission data during a plasma process. Analysis techniques provided by the invention investigate and discover the multiple complex correlations that form between various radiation emission wavelengths during a plasma process, and do not impose an expectation for a specific correlation or trend between the various wavelengths. The discovered correlations found to exist between the radiation wavelengths are then employed for monitoring a plasma process based on the discovered correlations. With this capability, the analysis techniques of the invention enable evaluation of interactions occurring across the entire spectrum of detected radiation emission wavelengths, and thus can accomplish detection and analysis of changes in a given plasma process due to shifts in the electrical and physical process environment as well as changes in a given process due to procession through stages of the process.

In the analysis techniques provided by the invention, the intensity of each of a number, P, of a plurality of radiation wavelengths that are emitted from a plasma process are monitored as the process proceeds. Indications of P-dimensional correlations between the intensities of the P monitored wavelengths are produced as the process proceeds. Then the produced correlation indications are compared with a prespecified correlation indication generated based on historical conditions for the plasma process, to determine the status condition of the process as the process proceeds.

Note that as explained above, this analysis does not impose an expected trend or wavelength intensity correlation template on an intensity value spectrum to analyze the status condition of the plasma process; instead, the analysis compares an indication of historically-based discovered correlations with an indication of the current correlation condition to determine the plasma process status condition.

In preferred embodiments, the radiation wavelengths that are monitored during the plasma process are between about 200 nm and about 800 nm. Preferably, at least 2 radiation wavelengths are monitored; more preferably at least about 10, at least about 100, or at least about 500 wavelengths are monitored.

The analysis techniques of the invention are particularly well-suited to various plasma processes and stages of plasma processes, including, e.g., plasma etch processes, and particularly, for determining when the endpoint stage of a plasma etch process is reached.

In embodiments of the analysis techniques provided by the invention, first a number, K, of historical plasma processes are carried out, during each of which the intensity of each of the P radiation wavelengths are monitored. Then the prespecified correlation indication is produced based on the intensities of the P monitored wavelengths for the process conditions of the K historical processes carried out. Alternatively, the prespecified correlation indication can be produced during the plasma process prior to the step of comparing the produced correlation indications with the prespecified correlation indication.

In other embodiments of the analysis techniques, the prespecified correlation indication can be updated based on the produced correlation indication, by, e.g., applying an exponentially-weighted moving average, based on historical process condition drift, to the prespecified correlation condition. Also, in a filtering process provided by the invention, the intensity of a number, J, of radiation wavelengths is monitored during the plasma process, with J>P, and the J monitored wavelengths are filtered to select those P wavelengths that each meet a prespecified intensity criterion.

In one embodiment of the analysis techniques provided by the invention, indications of the P-dimensional intensity correlations during a plasma process are produced as P-dimensional intensity correlation values. Here the step of comparing the produced correlation indications with a prespecified correlation indication is carried out by determining if each produced P-dimensional intensity correlation value is within a prespecified variation of intensity correlation values that is characteristic of historical process conditions for the plasma process. A produced intensity correlation value determined to not be within the prespecified variation of correlation values then indicates a change in the status condition of the process.

In a further embodiment of the analysis techniques provided by the invention, indications of the P-dimensional intensity correlations during a plasma process are produced as indications of maximum variations in correlations between the intensities of the P monitored radiation wavelengths. Here the step of comparing the produced correlation indications with a prespecified correlation indication is carried out by comparing the produced indications of maximum variations in correlations with prespecified maximum variation indications that are characteristic of historical process conditions. A produced indication of maximum correlation variation determined not to match a prespecified maximum variation indication then represents a change in the status condition of the plasma process.

In other embodiments, the above analysis techniques can be combined to produce a plasma process monitoring system having a selected sensitivity or a selected level of robustness to fluctuations of plasma process conditions over time.

The invention provides a range of systems for implementing the analysis techniques and for adapting the techniques to meet requirements of a selected plasma process to be monitored. Other features and advantages of the invention will be apparent from the claims, and from the following description and accompanying drawings.

BRIEF DESCRIPTION OF THE DRAWINGS

FIG. 9 is a flow diagram of an example plasma process monitoring technique employing the historical wavelength correlation indications produced by the flow diagram steps of FIG. 5;

FIG. 10 is a flow diagram of the steps for carrying out the endpoint condition evaluation step of FIG. 9;

FIG. 15 is a flow diagram of the step for carrying out the endpoint condition evaluation step of FIG. 14;

DETAILED DESCRIPTION OF THE INVENTION

Figure 1A:
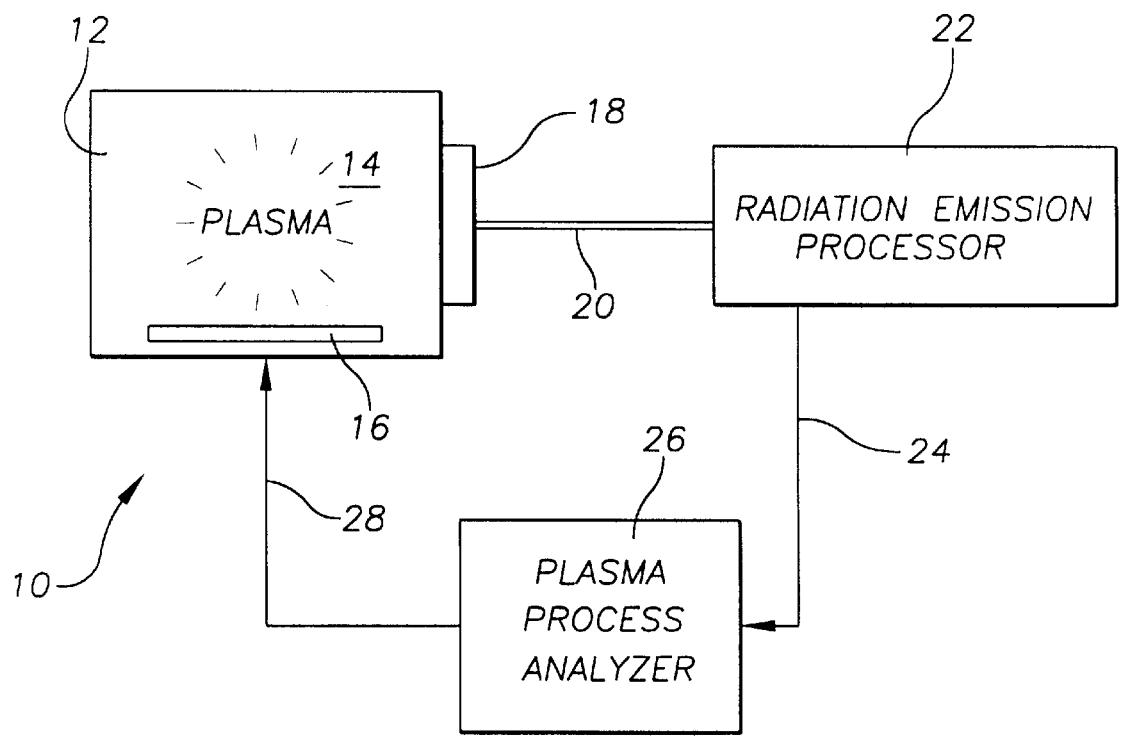
FIG. 1A is a block diagram of an example plasma process system arranged as a plasma etch system in accordance with the invention.

FIG. 1A shows an example plasma processing system 10, in block diagram form, arranged in accordance with the invention. In this system, which by way of example is a plasma etch system, a plasma etch chamber 12 is provided in a configuration suited for a given plasma etch application as is conventional in the art. The plasma etch chamber produces a plasma 14 of ionized reactant gases by application of RF power, transformer-coupled inductive power, or other suitable excitation means, to gases in the chamber, as is conventional, in the vicinity of a wafer 16 on which one or more layers of material are to be etched or which itself is to be etched, in a masked pattern as is conventional. A radiation port 18 in the chamber 12 is provided for connection of one or more optical fibers 20 to the port for collection of radiation emitted from the plasma 14. "Radiation" is here meant as any electromagnetic radiation emission generated during the plasma process that can be detected by a suitable detection system, and is not limited to visible wavelengths of radiation. As is conventional, multiple radiation ports can be provided in the chamber at various locations around the chamber for collecting radiation from various corresponding points in the plasma. Multiple optical fibers further can be arranged at the ports to collect radiation from different planes and angles in the plasma.

A radiation emission processor 22 accepts the radiation collected by the one or more optical fibers 20 and produces electrical signals 24 that indicate the intensity of the collected radiation at wavelengths detectable by the processor 22. The radiation emission processor thereby measures the intensity of the radiation emitted in the plasma, at the wavelengths to which the processor is sensitive. Preferably the radiation emission processor is configured to accommodate simultaneous processing of a number of distinct radiation wavelengths to be analyzed, hereinafter called wavelength channels, and preferably is sensitive to a large number, e.g., greater than at least about one thousand, wavelength channels.

The electrical wavelength channel intensity signals 24 are directed from the radiation emission processor to a plasma process analyzer 26 at which they are collected and stored for analysis. The plasma process analyzer provides both off-line and run-time, i.e., on-the-fly, processing capability for analyzing the wavelength channel intensity data to control the plasma chamber conditions by way of control signals 28 to chamber control systems such as the power system.

Figure 1B:
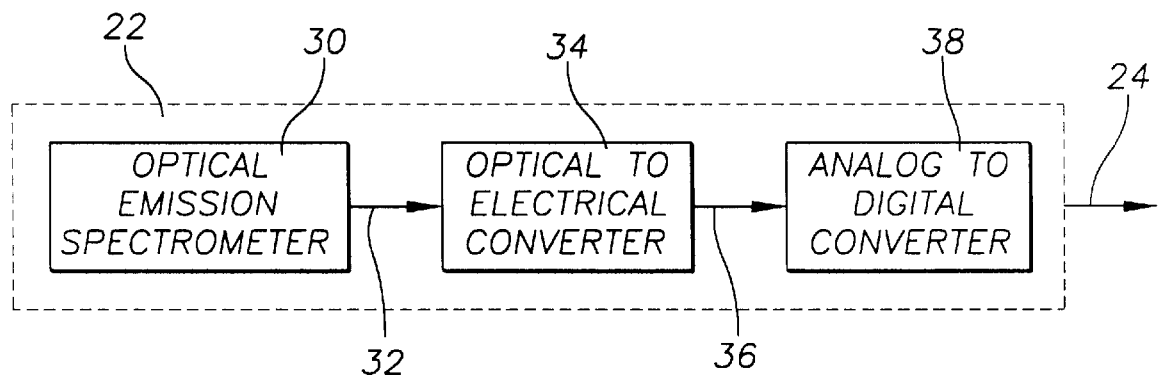
FIG. 1B is a block diagram of the radiation emission processor of FIG. 1A configured in accordance with the invention.

FIG. 1B shows, in block diagram form, components of one example radiation emission processor 22 in accordance with the invention. In this example configuration, directed to radiation emission analysis between about 200 nm and 800 nm in wavelength, the processor 22 includes a spectrometer, commonly known as an optical emission spectrometer 30, that resolves the wavelengths of radiation input to it to generate signals 32 indicative of each wavelength channel. An example commercially-available spectrometer is the SQ2000 optical emission spectrometer (OES) available from Ocean Optics, Inc., of Dunedin, Fla. This spectrometer is sensitive to UV, visible, and short-wave near-infrared wavelengths, depending on the resolution grating employed with the system; a sensitivity to wavelengths between about 200 nm and 1000 nm is generally capable.

Other commercial spectrometers, as well as custom-made spectrometers, are also suitable. Preferably, the selected OES system can resolve two closely-spaced atomic emission lines that are of particular interest for a given plasma process. In general, it is advantageous to employ an OES having a high spectral resolution. The Chromex OES system available from Chromex Inc., of Albuquerque, N.M., can monitor around 4000 distinct wavelength channels and for many applications, this degree of resolution may be preferable.

The radiation signals 32 are directed to a radiation converter, here called an optical-to-electrical converter 34 (O/E converter), such as a charge coupled device (CCD), that converts each radiation emission signal to a corresponding electrical signal 36 that is indicative of the intensity of the signal at that signal's wavelength. The Ocean Optics OES provides an accompanying CCD that is sensitive to about 86 photons per count. As can be recognized, high sensitivity is preferred for plasma process monitoring applications such as low open area etch scenarios in which highly sensitive monitoring capabilities may be required to detect any process changes. The electrical signal 36, which is inherently analog by nature, is then directed to an analog to digital converter 38 (A/D converter) which produces the digital electrical wavelength channel intensity signals 24 to be delivered to the plasma process analyzer 26. The Ocean Optics OES provides an accompanying A/D converter that is a 12-bit 500 kHz ISA board which can be directly plugged into a computer, e.g., a personal computer, to which the digital wavelength channel data is to be directed for analysis. As can be recognized, the electrical intensity wavelength data can be digitized using any suitable A/D architecture and speed that accommodates a given monitoring application.

The plasma process analyzer 26 is connected to the output of the radiation emission processor 22 in a convenient manner, as is conventional, to accept and store the wavelength channel data. A general purpose computer can be configured as the analyzer, with a convenient software language programmed to control the computer for data storage and analysis operations. Preferably, the computer is configured with a processor having capabilities that are at least comparable to the Intel 386DX processor with a math co-processor. A minimum of about 4 Megabytes of memory is preferable. Most preferably, the computer is configured with a processor having capabilities that are at least commensurate with that of the 100 MHz Intel Pentium processor, and having at least 8 Megabytes of memory. In general, more rather than less memory is preferred, and higher rather than lower speed processors are preferred to enable analysis of large amounts of wavelength data in real time during a process being monitored. Given a computer arrangement, one well-suited software environment for implementing the analysis techniques of the invention is the mathematical software processor called MATLAB, available from The MathWorks, Inc., of Natick, Mass. Other software environments, including programming languages such as the C programming language, can also be employed.

As can be recognized, custom-fabricated special purpose hardware, e.g., special purpose digital signal processing logic, can be produced to implement the functionality of a software configuration on a general purpose computer. Such an implementation can in many cases provide a great increase in computation speed over that of a computer. A trade off in cost, computing speed, system size, and other such factors thus is to be contemplated in implementing the plasma process analyzer for a given application.

With this implementation, in operation, as a plasma etch process is initiated and proceeds in the plasma etch chamber 12, the radiation emission processor 22 produces digital wavelength channel intensity data that is collected and stored in the plasma process analyzer 26. The analyzer evaluates the channel data in accordance with the techniques of the invention described below, and based on the analysis, determines the status of the plasma process, for use, e.g., to control the plasma chamber conditions in enabling reliable and repeatable process regulation.

As can be recognized, the implementation of optical computing techniques can be employed in an arrangement that eliminates the need for a radiation emission processor and that embodies the plasma process analyzer as an optical computation system or device. In such an arrangement, radiation emitted from the plasma chamber can be directly processed as optical signals for carrying out the analysis techniques of the invention to control the plasma chamber conditions. The invention in general contemplates the implementation of the plasma processing system of FIG. 1A in any convenient arrangement that best addresses a given application while providing the necessary functionality for analyzing wavelength channel intensity data in accordance with the techniques of the invention.

Figure 2:
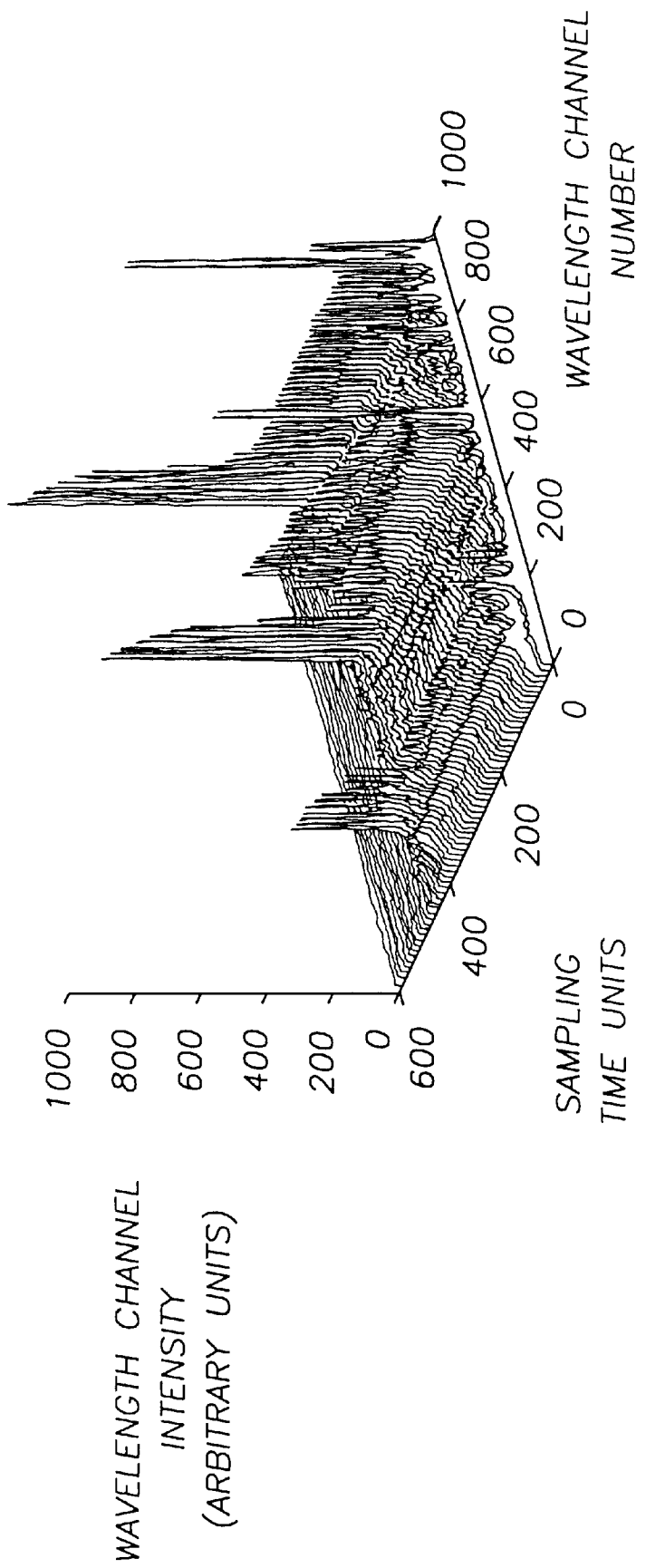
FIG. 2 is a plot of wavelength channel intensity found experimentally for 1000 wavelengths over 600 intensity sampling time units for a polysilicon plasma etch process.

These wavelength intensity channel data evaluation techniques provided by the invention are based on multivariate statistical analyses of multiple wavelength channel data. Specifically, the analyses evaluate changes in the correlations between wavelength channels as a plasma process such as a plasma etch proceeds. Referring to FIG. 2, which is a plot of wavelength intensity as a function of time for 1000 distinct wavelength channels during a plasma etch process, it is seen that correlations between the channels form and change during the course of the etch. This wavelength channel data was produced using an OES that sampled the intensity of 1000 distinct wavelengths every 600 milliseconds during a polysilicon plasma etch employing an etch chemistry of HBr:$Cl_2$ at a ratio of 5:1. The etch was carried out at a lower electrode RF bias power of about 50 Watts and inner and outer inductive coil power of about 524 Watts and 302 Watts, respectively, in a transformer-coupled power plasma etcher. The mean etch rate of the blanket polysilicon etch process was found empirically to be about 3200 Å/minute.

The time evolution of the intensity data shown in the plot is found to directly correspond to stages of the etch process. Initially an intensity transient is produced due to matching network tuning of the plasma excitation power and due to initiation of the RF bias power. After several sample time units, the intensity data is found to correlate with the main etch stage. As the polysilicon film is etched away during this stage, the intensity data is found to correlate with changes in the plasma chemistry. After about 350 sample time units, the wavelength intensity data is found to significantly change, in correlation with the endpoint of the main etch stage. Even though the plasma gas species are found to interact in a complex, nonlinear manner, clear channel correspondences appear. Specifically, wavelength channels corresponding to reactant gas species exhibit an increase in intensity as the main etch endpoint nears and less reactant is consumed; while wavelength channels corresponding to etch product species exhibit a decrease in intensity as the main etch endpoint nears and less etch products are produced.

Figure 3:
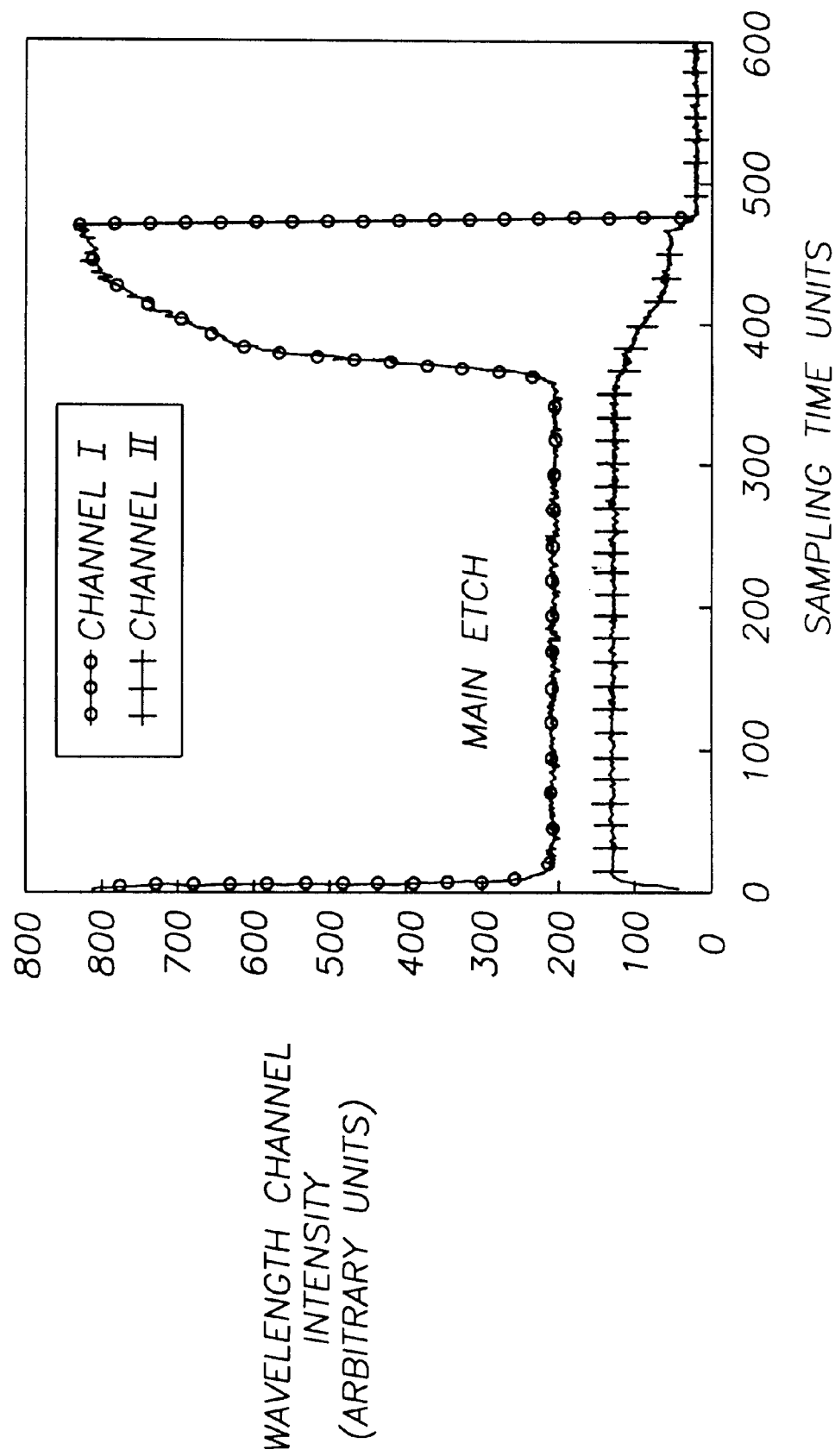
FIG. 3 is a plot of two of the wavelength channels plotted in FIG. 2.

FIG. 3 is a plot of intensity as a function of time for two wavelength channels that follow this process, taken from the plot of FIG. 2. The wavelength channel I dramatically increases in intensity at the start of the main etch endpoint condition, while the wavelength channel II decreases in intensity at the start of the main etch endpoint condition. Two chemical reactions representative of the polysilicon etch process known to result in these plot progressions are:

$$Si+Cl_2 \rightarrow SiCl_2, \tag{1A}$$

and

$$Si+2Cl_2 \rightarrow SiCl_4. \tag{1B}$$

Based on these etch reactions that are known and characteristic for the process, it is expected that as the main etch step ends, the wavelength channel intensity corresponding to the chlorine reactant gas species will increase and the wavelength channel intensity corresponding to the $SiCl_x$ etch product species will decrease. Although this specific and a priori expected inverse trend of the etch reactants and etch products can be an effective template for evaluating known and expected plasma etch conditions, it is found to typically be ineffective in advanced etch scenarios where the etch product concentration is very low, as in low open area etch applications. Specifically, it is found that the imposition of an a priori expected trend template on the plasma species generally fails to adequately detect plasma etch conditions in more advanced etch scenarios.

The wavelength intensity analysis techniques of the invention overcome the limitations of this restrictive technique by eliminating the use of a priori, expected, specific templates for wavelength channel data. Instead, the analysis techniques of the invention investigate and discover the multiple complex correlations that form between all the various wavelength channels in a set of channels, and do not impose an expectation for a specific correlation between the channels. The discovered correlations found to exist between the channels are then employed for monitoring a plasma process based on the discovered correlations. With this capability, the analysis techniques of the invention enable evaluation of interactions occurring across the entire spectrum of detected wavelength intensities, and thus can accomplish detection and analysis of changes in a given plasma process due to shifts in the electrical and physical process environment as well as changes in a given process due to procession through stages of the process.

Multiple analysis techniques based on this premise are provided by the invention. In a first example technique, considering a two-wavelength channel analysis in accordance with the invention, and referring to FIG. 4, during the steady state portion of a plasma process, e.g., a plasma etch stage, the measured intensity values of the two channels at each time step during the etch stage are found generally to cluster around a local region in 2-dimensional space defined by the intensity values of the two channels. Each point in the plot thereby represents the correlation between the two channels' intensity values; in other words, each point indicates the intensity value for wavelength channel two that occurred for a given intensity value for wavelength channel one at one of the time steps.

In accordance with the application of principal component analysis nomenclature, the intensity values 44 in the local region can be bounded by a confidence ellipsoid 45 that characterizes the correlation structure between the two channels for the etch stage. The long coordinate 46 of the ellipsoid 45 indicates the axis of maximum variance in the correlation, and defines the first principal component direction. The short coordinate 47 of the ellipsoid indicates the second principal component direction. The number of principal components and corresponding directions that can be determined is equal to the number of wavelength channels being considered, given sufficient channel data; there are accordingly two principal components for this two-wavelength channel example.

The characteristic ellipsoid and location are defined by its correlation, or covariance, structure. This correlation structure can be represented either directly, i.e., as a function of the measured channel intensities, or as a linear combination of values along the principal component coordinates, or directions. The invention contemplates plasma process analysis techniques that exploit either or both a direct representation and a principal component representation.

An intensity value point that is found to lie outside of the characteristic ellipsoid, e.g., intensity value 48 in the figure, indicates a statistically significant deviation from the stable correlation variation between the channels. This point represents a correlation between the channels that is not within the correlation variation characteristic of the two channels and spanned by the two principal components for the characteristic ellipsoid. Accordingly, the outlying point indicates the occurrence of some change in the process, e.g., a change in the process conditions away from the steady state process conditions, at the time during the process at which the intensity value is produced. Considering the analysis of a main plasma etch stage, the detection of such a change in multi-channel correlation can be employed in detecting endpoint of the stage.

Now extending this premise in accordance with the invention to a number, P, of wavelength channels to be analyzed, the intensity values of the P channels during the stable period of a given plasma process are found to generally cluster around a local region in P-dimensional space in an P-dimensional plot of the correlations between each channel and all of the other channels. A hyper-ellipsoid can be defined in the plot which bounds the local region to a given confidence level and can be represented by a corresponding number of P principal components, equal to the number of wavelength channels. The hyper-ellipsoid thus characterizes the correlations across all of the P channels for the given etch stage. A spectrum of intensity values that lies outside the hyper-ellipsoid indicates a statistically significant deviation from the stable P-dimensional correlation variation defined by the P principal components, and thus indicates the occurrence of a process change.

Note that as explained above, this technique does not impose an expected trend or wavelength channel correlation template on an intensity value spectrum to analyze the state of the plasma process; instead, the technique discovers what wavelength channel correlations exist and what variation in the correlations exists, and determines when an intensity value spectrum is found to statistically deviate from the correlation variation found to be characteristic for the process.

In accordance with the invention, an indication of the P-dimensional hyper-ellipsoid that is characteristic of the intensity data from P wavelength channels during a plasma process under consideration is produced using empirical data over the course of one or more historical runs or portions of the plasma process. Then, during a run or portion of a run of the plasma process to be analyzed, intensity data for the same P wavelength channels is produced in real time. With this data, the statistical composite function known as Hotelling's $T^2$ statistic is computed for the spectrum of P channels at each time step during the process, and the resulting time-dependent $T^2(t)$ statistic value is compared to a statistical upper control limit (UCL) value that is based on the historical data. The UCL defines the shape and size of the characteristic hyper-ellipsoid in P-dimensional space for the given etch stage with a single data value that can be compared with the single data value $T^2(t)$ statistic as-generated during the process at a given time, t. This comparison of the $T^2(t)$ statistic with the UCL is accomplished on-the-fly during the process being analyzed to detect a statistically significant deviation in multi-channel correlation variation and to produce for the corresponding time, t, an indication of a change in the plasma process.

Like the UCL, the $T^2(t)$ statistic function is based on historical intensity data, and specifically both are based on the mean and covariance of the historical data. As mentioned above, historical data is collected from a plasma process to be analyzed and using that historical data, variables to be used in computation of the UCL and the $T^2(t)$ statistic values are produced. One example plasma process that is particularly well-addressed by this analysis technique is the main etch stage of a plasma etch process. For this application, historical etch data from the main etch stage of a given plasma etch process is collected and processed to produce the mean and covariance data. Specifically, wavelength channel data is collected during the main plasma etch stage as that stage is carried out a number of times, K, during each of which the intensity of each of a number, J, of wavelength channels is individually monitored as a function of time, t, over a window of time duration T, using the plasma process arrangement described in connection with FIG. 1 above.

Figure 5:
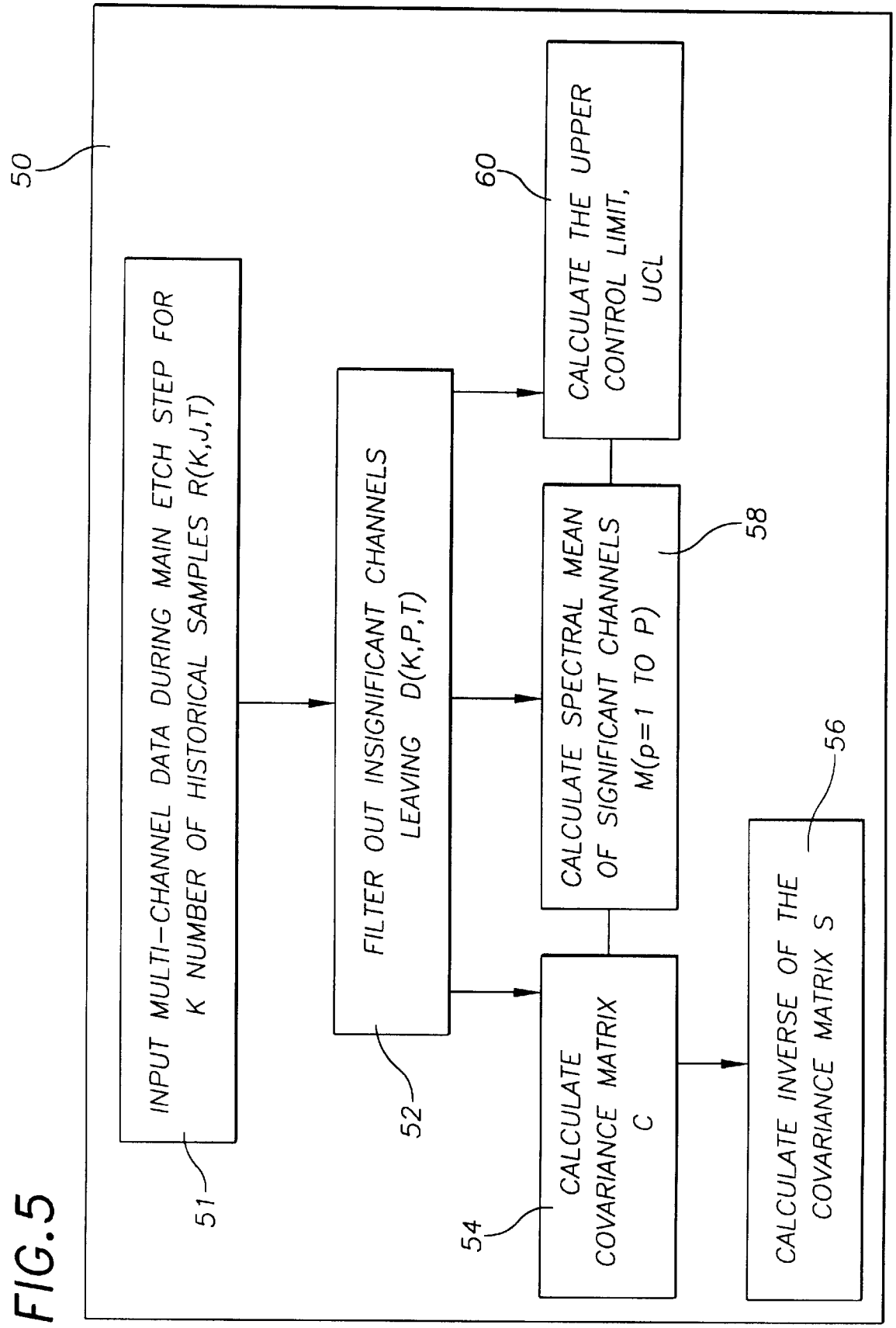
FIG. 5 is a flow diagram of a first example technique for producing historical wavelength correlation indications to be employed in a plasma process monitoring technique provided by the invention.

Referring to FIG. 5, in a first step 50 for producing historical statistical data to be used in the Hotelling's $T^2(t)$ analysis for endpoint detection of a main plasma etch stage, the wavelength channel intensity data for the J channels during each of historical K main etch processes over a time duration T is input 51 to the plasma process analyzer as a matrix R(K, J, T) of raw data. With this format, each row k of the matrix corresponds to one of the 1 to K experimental runs, each column j of the matrix corresponds to the intensity data for the $j^{th}$ channel out of J total channels, and each row-column layer of the matrix corresponds to a given time, t, during the time duration T. This matrix is filtered 52 to produce a data matrix, D(K, P, T), where P is equal to or less than J, for a selected number, P, of channels.

Then the corresponding covariance matrix C is computed 54 for the data matrix. The covariance matrix is a two-dimensional matrix of dimensions P×P that is computed based on all of the intensity data from all of the K historical runs for the time duration T. This matrix captures the dependence between the wavelength channels across the runs and the time duration. The inverse covariance matrix S, also a two-dimensional matrix of dimensions P×P, is then computed 56. Additionally, the mean intensity value, M(p=1 to P), of all the selected P channels across all of the K historical etch processes and across the time duration T is also computed 58, along with computation 60 of the upper control limit (UCL) that is characteristic of the intensity data for the selected P channels.

Figure 6:
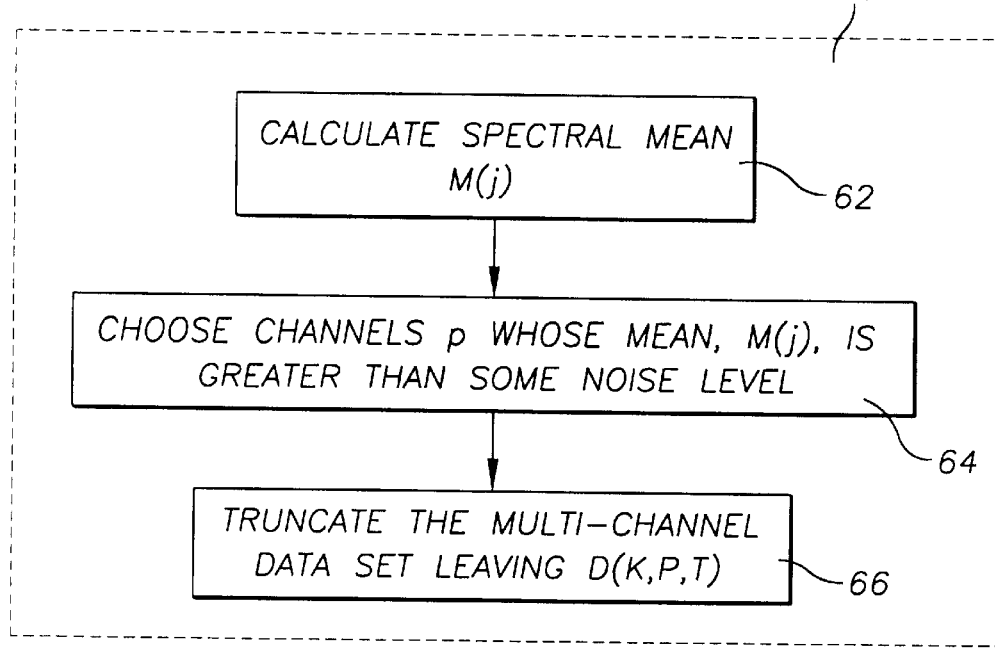
FIG. 6 is a flow diagram of the steps for carrying out the filtering step in the diagram of FIG. 5.

Referring also to FIG. 6, the step of filtering 52 the raw data matrix, R(K, J, T) is described in detail. This filtering step is intended to eliminate from analysis those wavelength channels that do not contain useful information so that unnecessary computational processing of the data is reduced. As can be recognized, any reasonable filtering standard can be employed or if desired, the filtering step can be eliminated. In one example filtering process, the intensity value mean, M(j), is computed 62 for each of the J wavelength channels taking into account all K processes and time duration T. Then only those P channels that each are characterized by an intensity value mean, M(j) which is greater than a specified threshold mean value corresponding to, e.g., a minimum valid signal and maximum allowable noise level, are chosen 64 for analysis. The rows of the raw data matrix R(K, J, T) are then truncated 66 to include only the P selected channel columns and thus to produce the data matrix D(K, P, T) for the selected P channels and the K main etch processes, for the time duration T.

As can be recognized, other filtering functions can be implemented. For example, low-pass filtering can be implemented to eliminate a portion of the noise spectrum; median filtering can be employed to eliminate intensity values that are severe outlying values; dead-band filtering can be implemented to force all intensity values that are around the mean to the mean value itself; or other suitable noise reduction techniques can be implemented.

Figure 7:
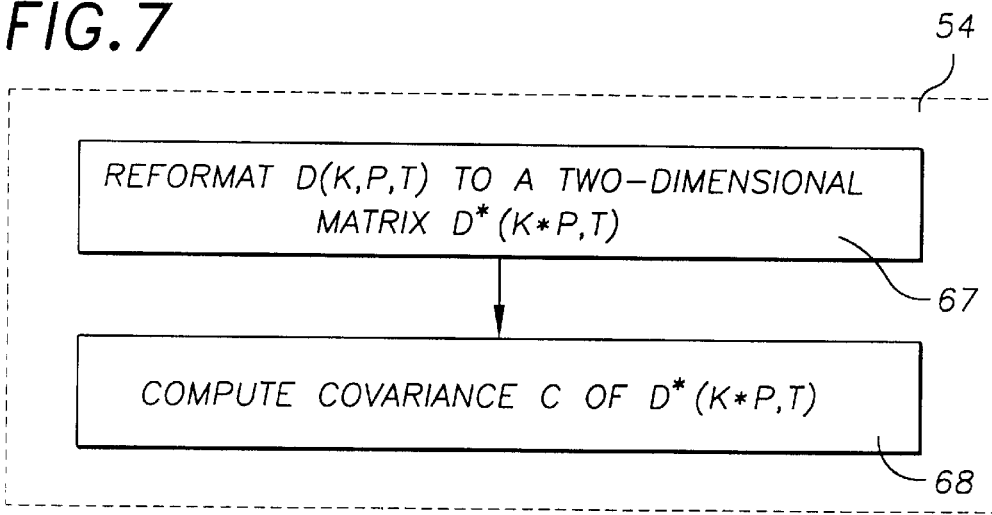
FIG. 7 is a flow diagram of the steps for carrying out the covariance calculation step of FIG. 5.

As shown in FIG. 7, the step of computing 54 the covariance matrix, C, is carried out by calculating the covariance of the data matrix D(K, P, T). First, the data matrix, D(K, P, T), is reformatted 67 as a two-dimensional matrix by treating all time samples as additional replicates of runs. That is to say, each time sample "layer" in D(K, P, T) is concatenated, in turn, onto the end of a two-dimensional matrix D*(K*T, P,), so that the total number of rows in the D* matrix is K process runs times T time samples, and the total number of columns in the D* matrix is P, corresponding to the number of selected channels. The covariance of the intensity values for the P channels over the total data rows, K times T, corresponding to the K etch main etch processes, is then computed 68.

Figure 8:
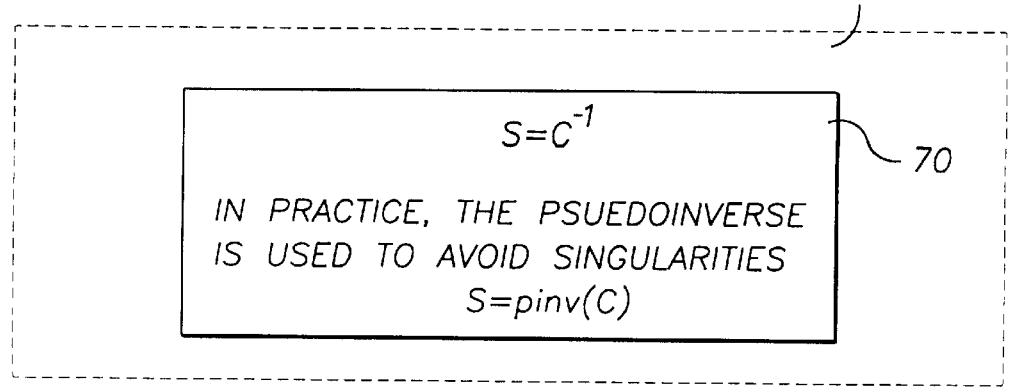
FIG. 8 is a flow diagram of the step for carrying out the inverse covariance calculation of FIG. 5.

Then, as shown in FIG. 8, the step of computing 56 the inverse covariance matrix, S, is carried out specifically by computing 70 the pseudo-inverse of the covariance matrix C. The pseudo-inverse computation is preferred because it is more efficient than a corresponding inverse computation, and avoids the possibility of generating a singularity due to singular value decomposition of a degenerate matrix. As can be recognized, the pseudo-inverse computation is not necessary, i.e., a true inverse computation is suitable, if a singular matrix is not produced.

Referring back to FIG. 5, the mean, M(P), of the intensity values of all selected channels, P, across all of the K etches, over the time duration T is computed 58, as explained above. Finally, the upper control limit (UCL) is computed 60 based on the historical data. In one example UCL computation technique, the F statistic is employed, with:

$$UCL = \frac{(K-1)(K+1)}{K(K-P)} F_{(1-\alpha, P, K-P)}; \tag{2}$$

where K is the number of historical main etch processes, P is the number of selected wavelength channels, a is the confidence level value, and the F statistic is employed in the conventional manner.

The value of the confidence level, a, sets the size of the hyper-ellipsoid in P-dimensional space that defines the general cluster of intensity values over the collection of channels and the collection of historical main etch processes. With a large number of selected channels, the F distribution can be approximated by a chi-squared distribution as conventionally implemented, whereby:

$$UCL = \chi_{\alpha, P}^2. \tag{3}$$

For example, with the number, P, of selected channels equal to 1000 and with a confidence level, α, of 99%, the UCL is 1107 based on relationship (3) above.

With this historical statistical computation completed, real-time plasma etch endpoint detection can be accomplished in accordance with the invention. Referring to the flow diagram of FIG. 9 and referring back to FIG. 1A, during the main etch stage of a plasma etch process, the intensity value data of a number of wavelength channels is produced by the radiation emission processor 22 and collected in the plasma process analyzer 26 as the etch proceeds. The number of wavelength channels employed can be selected based on computational efficiency required, computational speed required, and other such factors. It is found to primarily be limited by the number of distinctly resolved wavelength channels that can be produced by a given OES system, however; in other words, for all or most applications, it is preferable to employ all of the channels available from the selected OES system.

The OES system is configured to produce digital wavelength channel intensity data at selected intervals during the main etch stage, thereby defining analysis time steps during the process. The selected interval duration is preferably based on the desired speed at which the system can control endpoint. For example, if it is desired to control the etch chamber at the indication of endpoint condition within one tenth of a second of the occurrence of that condition, then it is preferred that the wavelength data sampling frequency be at least 10 samples per second. The sampling frequency for other maximum control delay requirements can correspondingly be determined.

At each sample time during the main etch stage, an intensity value matrix of raw data, R(J, t), is produced 76 for the group of J channels at time t; the matrix is a one-dimensional representation of all of the channel values at time t. This matrix is filtered 78 to produce a data matrix D(P, t), that includes intensity data at time t only for those P channels that were selected during the historical data collection phase. The data matrix for a given time, t, thus is formed of only intensity values for the P selected channels. The Hotelling's $T^2(t)$ statistic is then computed 80 for the data matrix D(P, t) for the time t as:

$$T^2(t) = [D(P, t) - M(P)] * S * [D(P, t) - M(P)]^T; \tag{4}$$

where the superscript T indicates transposition.

As explained above, the $T^2(t)$ statistic as given in expression (4) is a composite function that takes into account the covariation of the intensity value data across the selected channels. The $T^2(t)$ statistic represents a weighted generalized distance of the intensity value spectrum from the process correlation mean. In other words, at a given time, t, the $T^2(t)$ statistic indicates the distance between a point in P-dimensional space, corresponding to the correlations between the channels at that time, and the process mean of those correlations determined from the historical data.

Note that the $T^2(t)$ statistic can also be computed using generalized distances along the characteristic ellipsoid axis directions, because these direction simply establish a rotated coordinate system for the same data. The calculation of the $T^2(t)$ statistic can thus equivalently be performed using projections of the data onto all principal components or approximated using a subset of these components.

The Hotelling's $T^2(t)$ statistic as employed in accordance with the invention is based on an assumption that the intensity of each wavelength channel for one time sample is identically distributed to the intensity of that wavelength channel for the next time sample. The wavelength channel intensity data preferably do not take on a time series behavior during the etch being analyzed. Experimental wavelength channel intensity data generated during monitoring of a range of wavelength channels during various etch processes verified that indeed, for the plasma processes examined, the wavelength channels do not exhibit time-dependent behavior. It is thus understood that these assumptions are reasonable for many plasma process analyses. If it is found, however, that for a selected plasma process the wavelength channel intensities do take on a time series behavior, then the wavelength channel intensity noise can be "whitened" to essentially eliminate the behavior, or time-series "signatures" can be fit to the channel intensity data to enable computation of deviations from the "signatures" to obtain $T^2(t)$ statistic values.

Referring back to the flow diagram of FIG. 9, with the $T^2(t)$ statistic computed, the endpoint condition is evaluated 82 to determine if the endpoint of the main etch stage has been reached. As explained previously, as the endpoint is reached, the correlation between wavelength channels changes in some manner characteristic for that stage; as a result, the intensity value spectrum across the selected channels moves away from the P-dimensional hyper-ellipsoid defined by the selected channels' intensity values during the stable period of the main etch.

Endpoint is then defined as that time at which the channel intensity correlation decisively moves away from the defined hyper-ellipsoid, or stated another way, that time at which the P-channel intensity correlation is decisively outside of the correlation variation characterized for the historical data. Computationally, this is indicated when the $T^2(t)$ statistic decisively increases to a value greater than the UCL value previously calculated. The UCL thus is the metric for setting a limit in the variation of intensity value correlation above which a channel spectrum is deemed to fall outside of the typical process correlation variation.

A variety of conditions can be imposed to detect a decisive increase in the $T^2(t)$ statistic value above the UCL value, as can be recognized. In one example condition, endpoint is not indicated unless the $T^2(t)$ statistic value is greater than the UCL value for a minimum number of evaluation events. Referring to FIG. 10, the endpoint evaluation step 82 is in this example carried out by first setting 84 the value of a counter, c, to zero. Next the current counter value is compared to a prespecified maximum counter value, $c_{max}$. The maximum counter value is selected based on, e.g., the level of confidence expected for a given main etch process and thus can range from the value of one to a higher integer value, e.g., four. In the next step, the current counter value is compared 86 to the maximum counter value. If the current counter value is greater than the maximum counter value, endpoint detection is indicated 88.

If the current counter value is not greater than the maximum counter value, then the current $T^2(t)$ statistic value is compared 90 to the prespecified UCL value. If this comparison indicates that the $T^2(t)$ statistic value is greater than the UCL value, then the counter is incremented 92; otherwise, the counter is reset 84 to zero. This evaluation loop implements a condition requiring an increase in the $T^2(t)$ statistic value above the UCL value for more than a number, $c_{max}$, of evaluation events before endpoint is indicated, and can be adjusted to correspond to a confidence level for a given etch process.

Upon such indication, the plasma process analyzer 26 (FIG. 1) signals the controller of the plasma etch chamber 12 of endpoint, whereby the chamber conditions are adjusted for a next etch stage, e.g., an over-etch stage. The plasma process analyzer is then reset for analysis on the next stage of the current etch process or for analysis on the next etch process to be undertaken.

EXAMPLE I

The endpoint detection technique described above with regard to the flow diagrams of FIGS. 5–10 was employed to determine the endpoint of the main etch stage of a blanket polysilicon plasma etch process. The etch was carried out on a Lam Research Transformer-Coupled Plasma Etcher modified for two-coil operation. The inner coil etch power was set at about 524 Watts; the outer coil etch power was set at about 302 Watts; the lower electrode bias etch power was set at about 50 Watts; and the reactive plasma was an $HBr:Cl_2$ chemistry in a ratio of about 5:1. The etch rate under these conditions was found to be about 3200 Å/minute. The radiation emission processor was implemented as the model SQ2000 OES system from Ocean Optics, Inc. as described above. The system was configured to sample and produce intensity value channel data every 600 milliseconds. The plasma process analyzer was implemented as a general purpose computer with a 90 MHz Intel Pentium processor on which was programmed the MATLAB software process environment from The MathWorks, Inc. to implement the analysis steps.

Two historical etch runs were carried out each with intensity value data from 1000 channels without the use of filtering; i.e., the covariance and mean matrices were produced for K=2 and J=P=1000. The confidence level, α, employed to compute the UCL, was set at 99%, for a UCL of 1107 based on a chi-squared distribution.

Figure 11A:
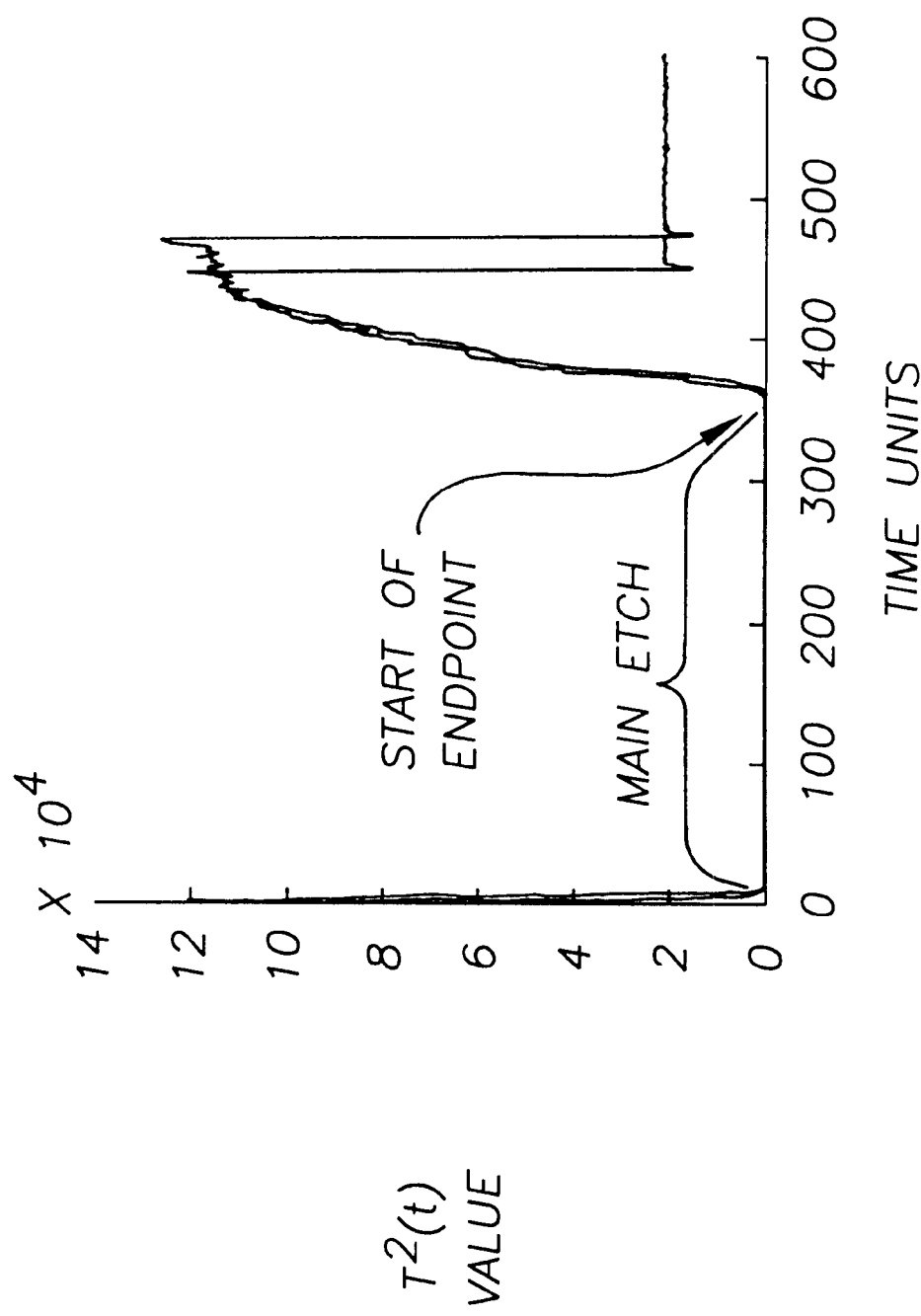
FIGS. 11A and 11B are plots of the Hotelling's $T^2(t)$ value as a function of time during an experimental polysilicon plasma etch process, produced in accordance with the invention to correctly detect the start of endpoint during the etch.
Figure 11B:
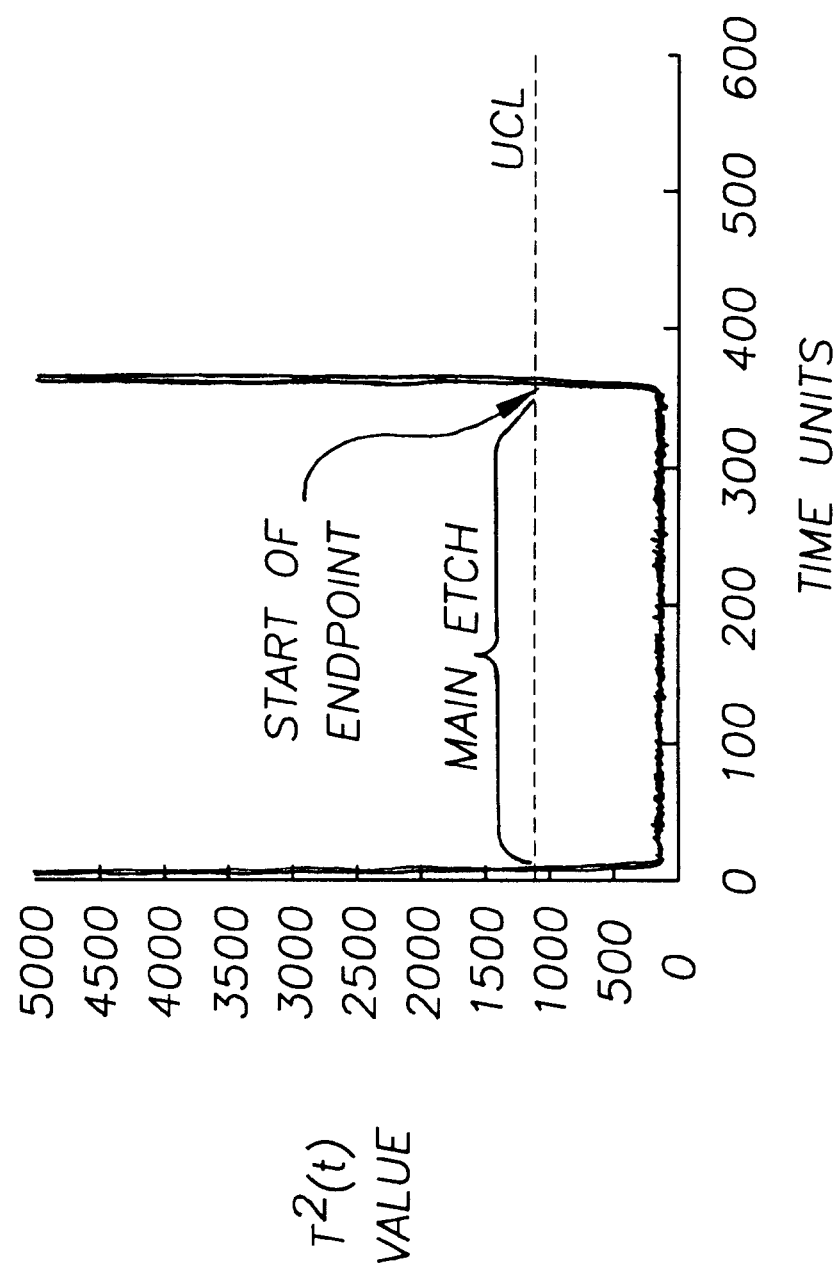

FIGS. 11A and 11B are plots of the $T^2(t)$ statistic value computed during the main etch stage of the blanket polysilicon etch process; FIG. 11B provides a finer $T^2(t)$ statistic value scale for the same data plotted in FIG. 11A. Each plot includes two data curves each corresponding to a separate etch process. The $T^2(t)$ statistic values plotted are based on mean and covariance data computed for the two historical runs described above. An initial transient was observed due to the initial stages of the etch including a power matching stage, and so the initial 50 computed $T^2(t)$ statistic values, corresponding to a time duration of about 30 seconds, were ignored during the real-time endpoint evaluation process.

The plots indicate that after the initial transient, during the steady state main etch stage the $T^2(t)$ statistic value is very small. This indicates that during the steady state of the main etch stage the measured correlation between wavelength channel intensities is very close to the historical intensity mean for the process and does not fall outside of the historical characteristic correlation variation. At the onset of endpoint, the $T^2(t)$ statistic value dramatically increased; indeed, as shown clearly in FIG. 11B, the statistic value approaches a step function as it rises above the UCL at the start of the endpoint condition. This indicates that at the start of endpoint, the measured correlation between wavelength channel intensities is significantly outside of the historical characteristic correlation variation for the main etch stage. This experiment verifies the ability of the technique to clearly distinguish an endpoint condition from earlier points in the main etch stage based on a measurement of deviation from historical correlation variation.

The signal to noise ratio for this endpoint detection example can be computed based on the $T^2(t)$ statistic value. The signal factor value is taken to be the difference between the value of the $T^2(t)$ statistic after much of the polysilicon film clears during endpoint and the value of the $T^2(t)$ statistic before endpoint is reached. The noise factor value is taken to be the standard deviation of the $T^2(t)$ statistic value during the stable, steady state period of the main etch stage. With this metric, the signal to noise ratio (S/N) for the endpoint detection technique of the invention applied to the blanket polysilicon layer etch is about 3000.

This extremely high signal to noise ratio is in great contrast with that of conventional endpoint detection techniques that rely on intensity value data from only one or two wavelength channels. Considering the two-channel data plotted in FIG. 3 for a blanket polysilicon etch process, it is found that the S/N for wavelength channel I is about 150. The Hotelling's $T^2(t)$ analysis applied in accordance with the invention to a range of wavelength channels is thus seen to enable an increase in S/N by a factor of about 20.

EXAMPLE II

Intensity value data was collected for 1000 wavelength channels during the plasma etch of an oxide layer that was masked with a deep UV photoresist in a pattern containing only about 1–1.5% open exposed area to be etched. The etch was carried out in an Applied Materials plasma etcher using a proprietary etch process recipe. The radiation emission processor and the plasma process analyzer were implemented as in Example I above. The historical data analysis and the measured data conditions were also as in Example I above.

Figure 12:
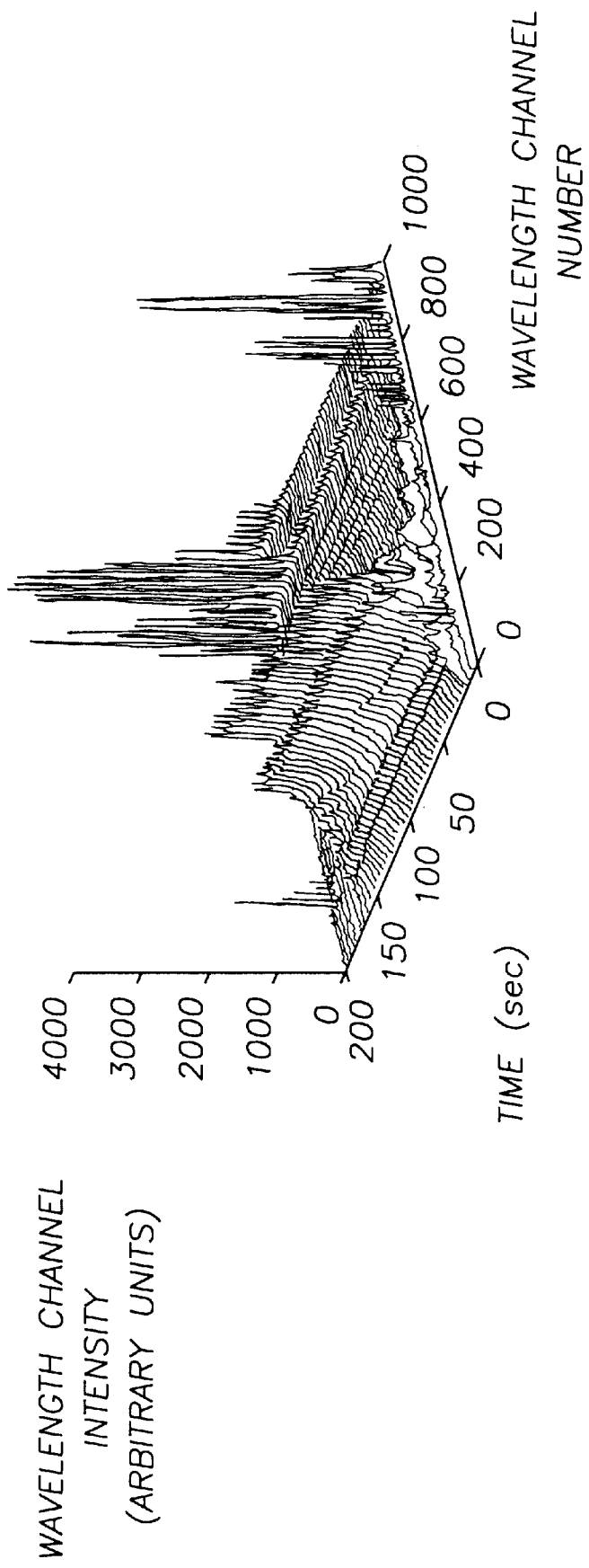
FIG. 12 is a plot of wavelength channel intensity found experimentally for 1000 wavelengths over 200 seconds for an oxide plasma etch process.

FIG. 12 is a plot of intensity of the 1000 wavelength channels as a function of time during the oxide etch process. The plot shows a correspondence to the multi-stage process in which an argon chemistry is first used to strike a plasma, a second chemistry is used to etch the anti-reflective coating from the photoresist, and a $C_2F_6$ chemistry is used during a main etch stage to etch the oxide.

It was found that using conventional techniques, automatic endpoint detection was very difficult for this plasma etch system because the internal etch chamber walls are quartz and thus the walls are reactive to plasma reactant gases employed in oxide etch recipes. The endpoint of the main etch stage of an oxide plasma etch under such conditions must therefore be detected even while the chamber liner continues to etch; in other words, the component of the intensity value data that relates to the main etch process is reduced by an amount that is a function of the amount of chamber wall etching.

The low open area oxide etch was analyzed using the endpoint detection technique as-implemented in Example I above. At the channel filter step during the historical data collection phase, it was found that of the 1000 initial wavelength channels, 759 channels exhibited a mean intensity value of more than about 100 in arbitrary units, which was set as a noise ceiling. A confidence level of 99% was used to produce a UCL value of 853 for the 759 selected channels based on a chi-squared distribution.

Figure 13:
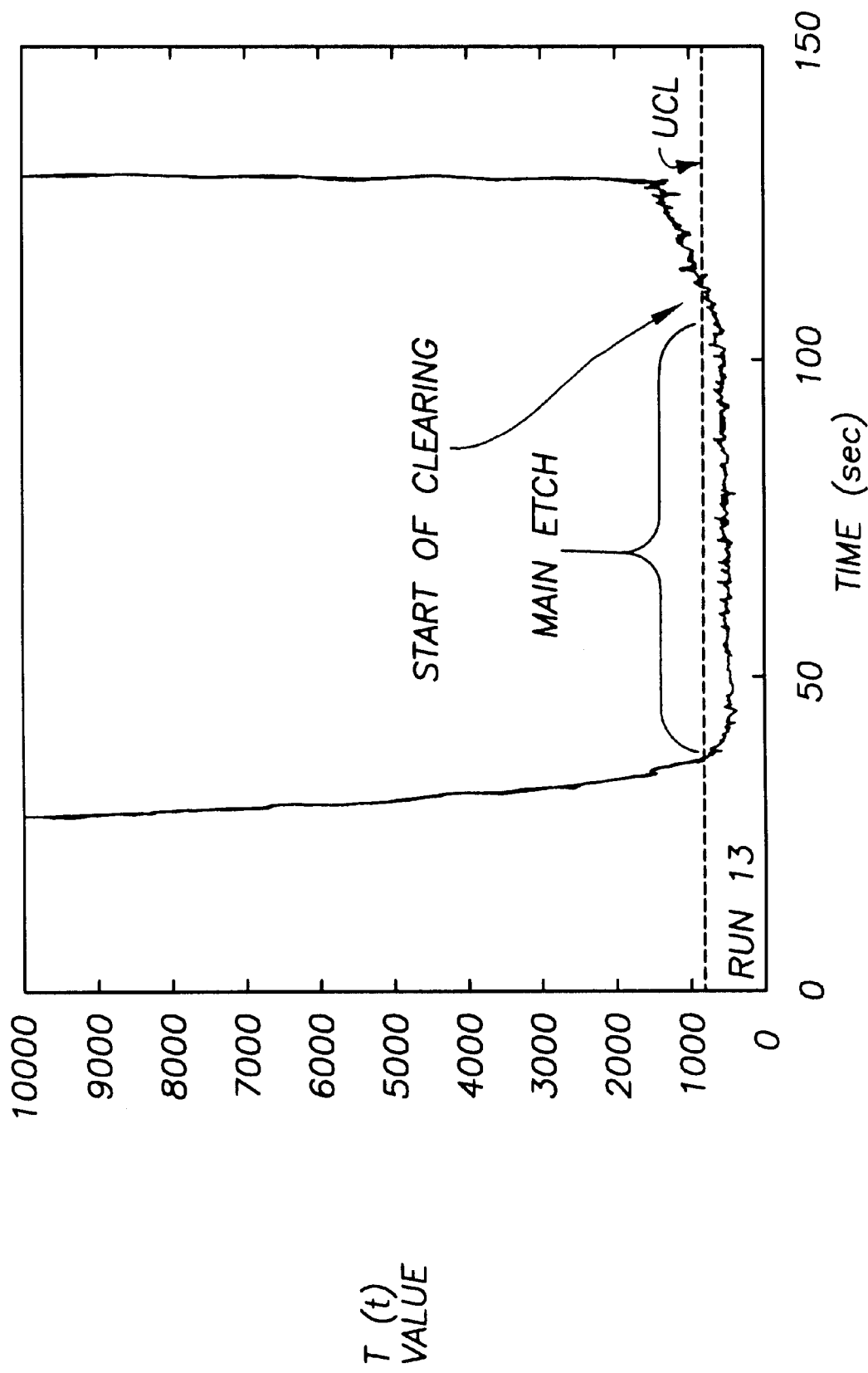
FIG. 13 is a plot of the Hotelling's $T^2(t)$ value as a function of time during an experimental oxide plasma etch process, produced in accordance with the invention to correctly detect the start of endpoint during the etch.

During the etch process, the intensity values of the wavelength channels were collected at a frequency of about 5 Hertz, with an integration time of about 15 milliseconds. FIG. 13 is a plot of the $T^2(t)$ statistic value as a function of time during the etch process.

During the main etch step, the $T^2(t)$ statistic value remained below the UCL value, and the $T^2(t)$ statistic value definitively increased beyond the UCL value at a time found to coincide with the endpoint of the main etch. This indicates that the endpoint detection technique of the invention is sensitive enough to detect endpoint even for extremely low open area etch patterns; indeed, the technique is as effective in this low open area case as it was for the blanket etch case.

The invention contemplates a range of variations in the analysis technique employed in the examples and description presented above. As previously explained, the analysis can be adapted for detecting the status condition of plasma etch processes other than a main plasma etch stage, and can be adapted for detecting the status condition of plasma processes other than plasma etch processes. For a selected analysis application, the covariance and mean of the intensity values from at least two radiation emission channels are computed for the selected application to characterize the channel correlation and correlation variation for the application. Then an appropriate evaluation condition is selected, in the manner of the endpoint condition evaluation step given above, to produce an estimate of the probability of or the detection of a process change outside of the correlation variation found for the historical analyses.

In addition, the historical statistical analysis steps of FIGS. 5–8 can be embodied in a real-time analysis that is completed during a given process to be analyzed. For example, in the case of detection of endpoint of a main plasma etch stage, the historical statistical analysis can be completed once steady state conditions are established at the start of the main etch stage, rather than off-line at a time previous to the process run under analysis. As can be recognized, the historical statistical analysis steps can be adapted in other ways to accommodate other run-time capabilities desirable for a given application.

The plasma process analysis technique can also be adapted to provide an indication of degree, or percentage, of the onset of a selected process condition, such as an etch endpoint condition across a wafer being processed. In such a scenario, if, e.g., across a wafer 80% of a layer being etched has reached endpoint of the etch, a result of 0.8 would be provided. This capability can be implemented in accordance with the invention by, e.g., implementing a Bayesian estimate of the probability of a given $T^2(t)$ statistic value not belonging to a current $T^2(t)$ statistic value distribution that is based on the $T^2(t)$ statistic values computed during the run. This probability measure can then be employed as a non-discrete measure of a degree of certainty as to whether endpoint has occurred. This technique can be adapted to employ more than the current $T^2(t)$ statistic value; the $T^2(t)$ statistic value for several previous time samples, e.g., $T^2(t-s)$, $T^2(t-s+1)$, etc., where $0<s<t_{current}$, can instead be employed.

In a further adaptation of the technique, a $T^2(t)$ statistic value can be computed based on a time-series of wavelength channel intensity values collected during a moving window of time as a plasma process proceeds. The analysis steps described above are here directly applicable, with a process condition indication, such as the indication of endpoint of a main plasma etch stage, being generated based on a given time window of wavelength channel intensity values rather than a single time sample of such values.

In accordance with the invention, the plasma process analysis technique can further be adapted to reflect drifts in a plasma process over time. Such adaptation is particularly important for plasma etch endpoint detection, where even slight process changes can dramatically reduce the ability to credibly detect etch endpoint. By "process drift" is here meant slow fluctuations in process conditions, i.e., process conditions that change over the course of several processes. These changes can reverse direction over time, as is known. Process fluctuations over the course of several runs can be due to, e.g., polymer build-up on the plasma chamber radiation ports, etching of the plasma chamber walls, contamination of the plasma chamber by wafer materials, and other such process environment variations. Such variations do not necessarily act as neutral intensity filters, and instead can result in wavelength-dependent intensity changes as well as wavelength-dependent channel correlation changes. As a result, over time, such variations can be manifested as unpredictable drifts in the intensity values of plasma radiation emissions. In terms of the P-dimensional hyper-ellipsoid described above for characterizing an etch stage, the hyper-ellipsoid can be found to drift in the P-dimensional space over time, i.e., the wavelength channel intensity mean value and covariance matrix can be found to fluctuate over time.

The invention contemplates a range of techniques for accommodating such drift, by, e.g., averaging, filtering, smoothing, or suitable prediction methods. In one example technique in accordance with the invention, a moving average, such as an exponentially-weighted moving average, is employed to update the mean and covariance factors employed in the Hotelling's $T^2(t)$ analysis in a manner that corresponds to the drift.

Figure 14:
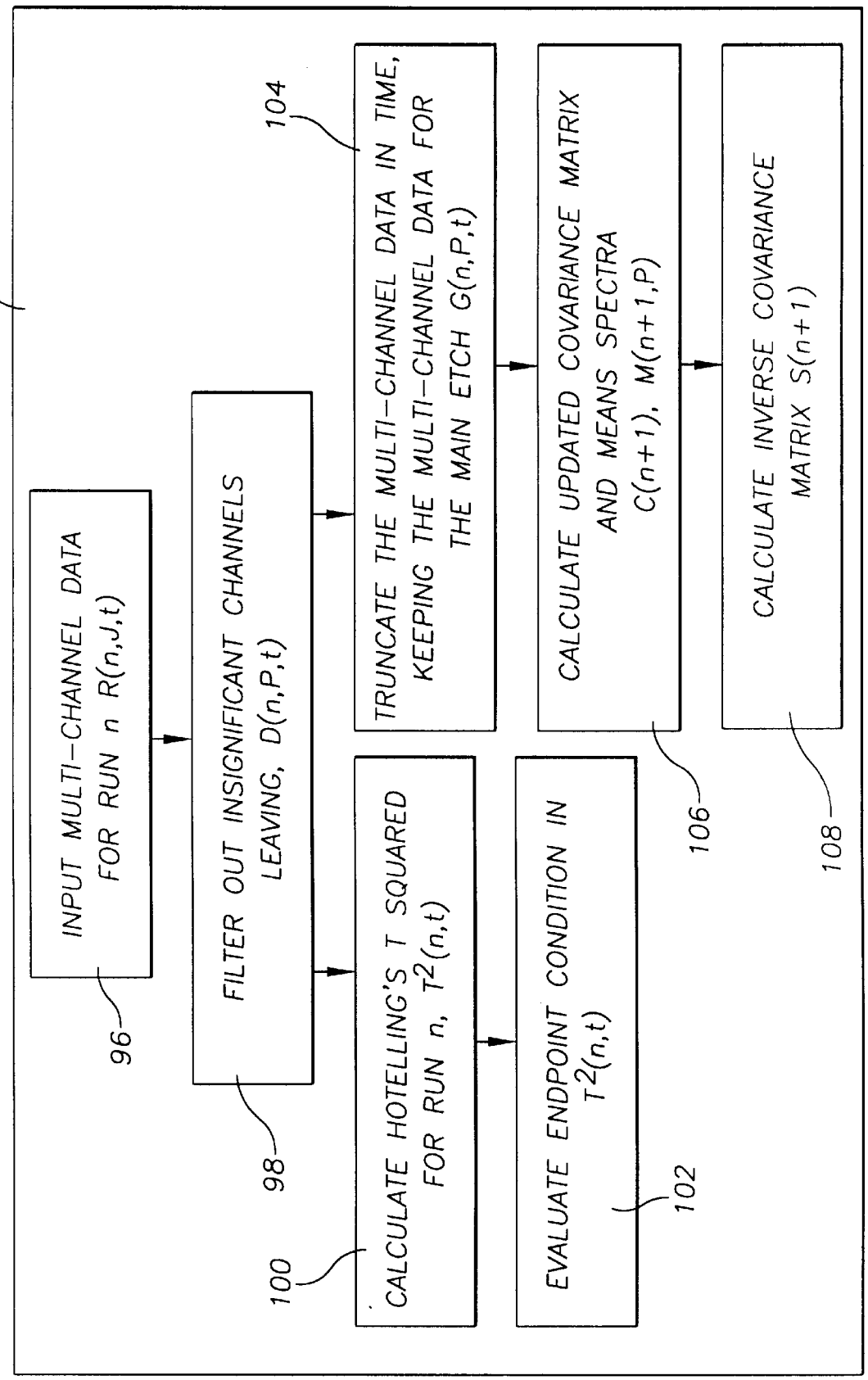
FIG. 14 is a flow diagram of a technique provided by the invention for updating the plasma process monitoring technique of FIG. 9 based on plasma process fluctuations occurring over a sequence of process runs.

In this example, and referring to the flow diagram of FIG. 14, for a given etch process, e.g., a main etch process, to be analyzed for, e.g., endpoint condition, and that is a number, n, in a series of N etch processes to be carried out, e.g., in a series of N wafers being etched sequentially, the analysis technique of the invention provides for $T^2(n, t)$ analysis that is based on the position of the given etch process in the series. With the historical statistical computation completed to obtain the inverse covariance and mean factors for the $T^2(n, t)$ computation, in a first step of the analysis 95, for each time step during the main etch stage, an intensity value matrix of raw data, R(n, J, t), for the current process, n, is produced 96 for the group of J wavelength channels being analyzed at each time t in the manner previously described. This matrix is filtered 98 to produce a data matrix D(n, P, t), for process n that includes intensity data only for those P channels that were selected during the historical data collection phase. The data matrix for a given time, t, thus is formed of only intensity values for the P selected channels.

The Hotelling's $T^2(n, t)$ statistic is then computed 100 for the data matrix D(n, P, t) of etch process n. Referring also to FIG. 15, the statistic value is computed 110 for the time t as:

$$T^2(n, t) = [D(n, P, t) - M(n, P)]^* S(n)^* [D(n, P, t) - M(n, P)]^T; \quad (5)$$

where the superscript T denotes a transposition. The mean, M(n, P), and inverse covariance, S(n), employed in the function can be determined based on historical data analyzed at some point in the past or can be adjusted factors obtained in a manner explained below.

With the $T^2(n, t)$ statistic value computed, the endpoint condition is evaluated 102 in real time to determine if the endpoint of the main etch stage has been reached during etch process n, based on a comparison of the $T^2(n, t)$ statistic value with the UCL computed from the historical data. As explained above, a conditional evaluation can be employed to determine when a decisive increase in the $T^2(n, t)$ statistic value above the UCL has occurred, corresponding to start of the endpoint condition. The evaluation steps 82 of FIG. 10, explained previously, or other suitable evaluation process, can here be used. When the main etch stage endpoint is detected, the plasma chamber control systems are alerted to the condition to halt the main etch process, as explained above.

Now referring back to FIG. 14, prior to the start of a new etch process to be analyzed, the mean and covariance factors from historical data are updated to reflect the conditions of the most recent process run as well as that of previous process runs. In this update technique, the filtered data matrix, e.g., D(n, P, t) for the most recent process run, is retained in memory. Each filtered data matrix is truncated 104 to ensure that it includes only data from the etch process stage of interest, e.g., the main etch stage. The data matrix may have also included data from earlier stages, if data collection during previous analyses took place during the entire etch process. The truncating can be accomplished based on known time correspondences for the etch stage of interest, or other such correspondence, to produce a truncated matrix, e.g., G(n, P, t), for the most recent process run, process n.

With the truncated matrices from previous process runs, e.g., G(n, P, t), produced, the covariance matrix and the mean factor are updated 106 to produce an updated covariance matrix factor, C(n+1), and an updated mean factor, M(n+1, P), to be used for the next process analysis, e.g., the n+1 etch process in the series of N processes being analyzed. The corresponding inverse covariance matrix, S(n+1), is then computed 108 to complete the factors needed for computing the $T^2(n+1 t)$ statistic value during the n+1 process analysis.

Figure 16:
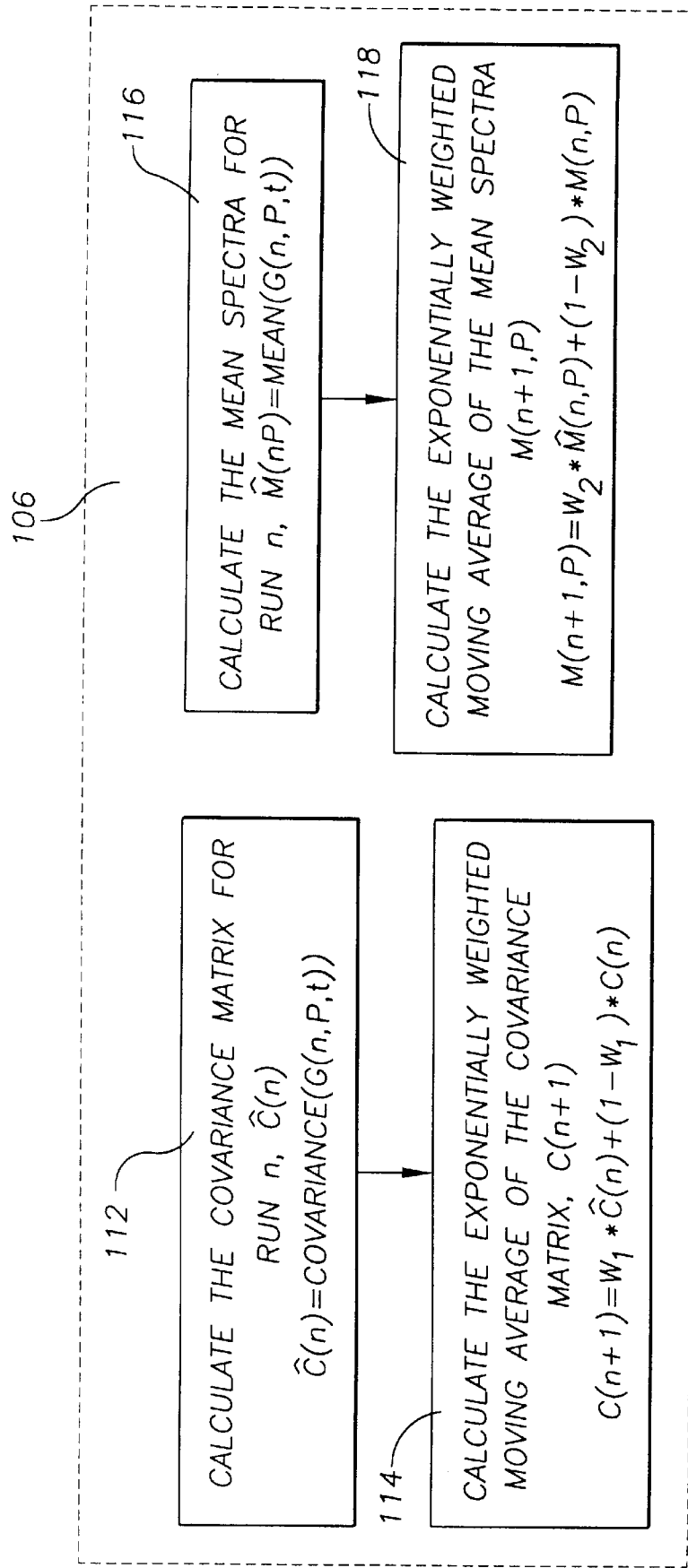
FIG. 16 is a flow diagram of the steps for carrying out the covariance and mean update calculation step of FIG. 14.

Referring to the flow diagram of FIG. 16, the updated covariance and mean factors to be employed in the n+1 process analysis are computed based on the truncated matrix G(n, P, t) for the most recent process analysis. Specifically, the updated covariance is computed by first calculating 112 the measured covariance matrix, $\hat{C}(n)$, for the truncated matrix G(n, P, t) from the P channels of intensity data during process n over the duration of the main etch. Then the updated covariance is computed 114.

As explained above, the invention contemplates a range of techniques for updating the covariance and mean factors. For the example of an updating function embodied as an exponentially-weighted moving average (EWMA), the EWMA is applied to the measured covariance matrix computed for run n, $\hat{C}(n)$. Here a factor weight matrix, $W_1$, is selected of dimension P×P and includes diagonal element values that are selected to reflect the degree of fluctuation occurring in the process environment, and range between zero and one. Diagonal values closer to the value one are selected for strong process fluctuation, i.e., when a strong update impact is desired, while diagonal values closer to the value zero are selected for slower process fluctuation, i.e., when a weak update impact is desired. The particular diagonal value chosen preferably reflects an estimate of both the amount of drift and the amount of noise characteristic of the process. With the EWMA weight matrix diagonal values set to zero updating the computation reverts to the technique described above employing no update.

The updated covariance for the next analysis, i.e., the analysis of the n+1 process, is then given as:

$$C(n+1) = W_1 \hat{C}(n) + (1-W_1)*C(n); \qquad (6)$$

where C(n) is the covariance matrix that was employed for the current n process analysis, and is distinct from that measured based on the truncated matrix G(n, P, t) at the end of the process. This updating function results in a weighting of the most recent process run conditions most strongly, with previous process run conditions weighted less strongly, thereby reflecting the fluctuation trend in the process conditions over time.

To compute the updated mean factor, the mean for the most recent process, $\hat{M}$(n, P) is first computed 116 (FIG. 16) by computing the mean of the truncated matrix, G(n, P, t). Then a second EWMA factor weight matrix, $W_2$, similar in form to the first weight matrix, $W_1$, is here applied 118 to the computed mean to produce an updated mean as:

$$M(n+1,P) = W_2 * \hat{M}(n,P) + (1-W_2)*M(n,P). \qquad (7)$$

As with the covariance update relationship, this mean update relationship reflects the trend in process fluctuation, or drift, over time by weighting the most recent process analysis conditions more strongly than previous process analysis conditions. Note that the two EWMA factor weight matrices can be identical or can take on distinct values.

Figure 17:
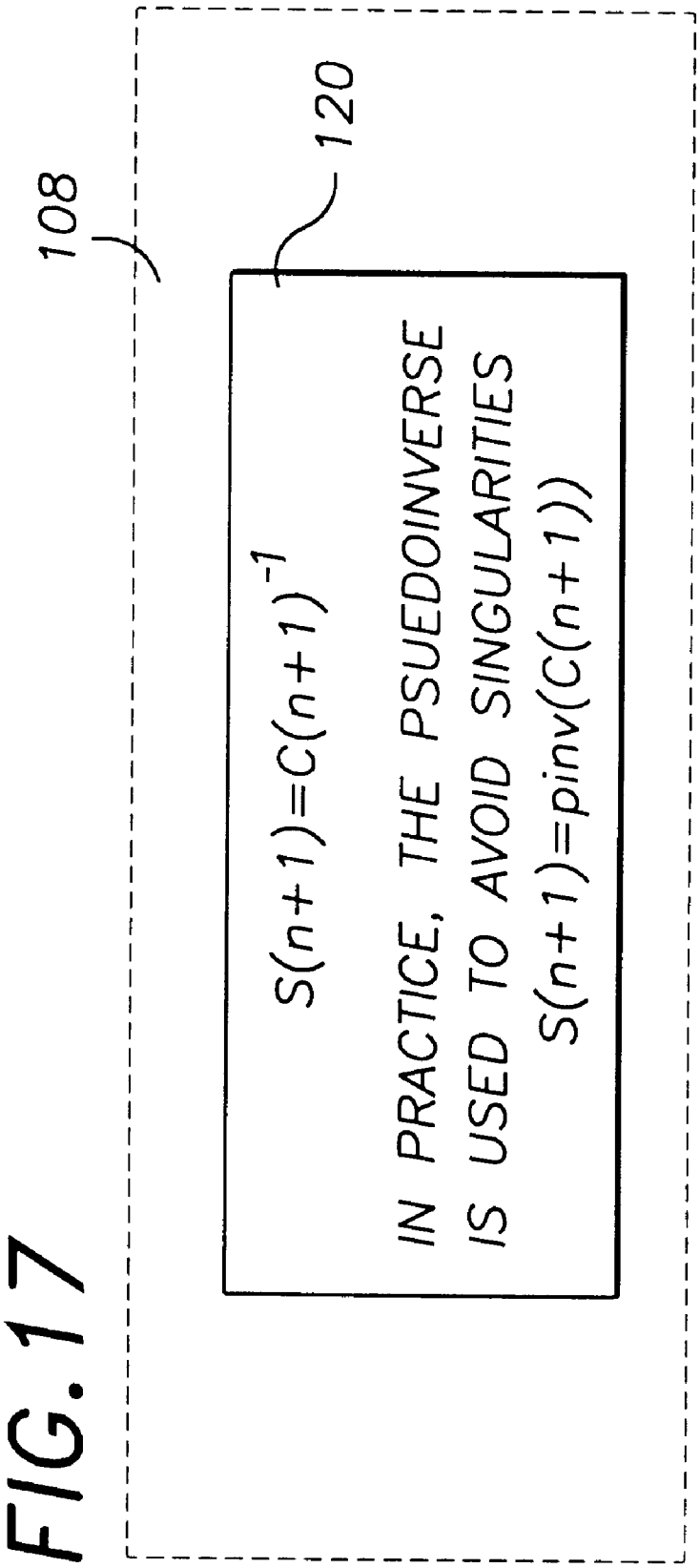
FIG. 17 is a flow diagram of the step for carrying out the inverse covariance calculation step of FIG. 14.

Finally, an updated inverse covariance factor is computed 108 as given in FIG. 17. Here the updated inverse covariance is computed 120 as the pseudo-inverse to avoid the occurrence of singularities in degenerate matrices. With the historical factors updated, the endpoint analysis technique 95 of FIG. 14 is then undertaken, as described above, for the N+1 process analysis.

As can be recognized, this example update adaptation of the analysis technique can be applied in real-time during analysis of an etch stage being monitored. Updated covariance and mean factors can be produced using intensity data from a first portion of the etch stage as the etch progresses. The updated factors can then be employed for a $T^2(t)$ analysis during a second portion of the etch stage. The adaptation technique can also be applied to detection of other stages beyond the main etch stage of a plasma etch process, and in general to other plasma processes, by employing intensity value data from the etch stage or process of interest in the manner described above.

The invention contemplates additional updating mechanisms beyond an EWMA updating mechanism. For example, low-pass, band-pass, or notch filtering, median or other nonlinear filtering, or other suitable technique, including prediction techniques, can be employed. In one example, a double-exponentially weighted moving average (DEWMA) is employed to produce updated mean and covariance factors for a future process analysis. In this technique, an EWMA of the value of each factor and an EWMA or the slope, or trend, of each factor, is employed in the update; each factor is updated based on the sum of the EWMA of the value of each factor and the EWMA of the trend of each factor. These updates replace the EWMA updates 114 and 118 in step 106 described above.

As with the mean and covariance factors, the upper control limit can be adjusted to reflect changes in a process. For example, if it is found by diagnostic measurements that the analysis technique is prematurely indicating the onset of endpoint of a main etch stage, then the upper control limit can be increased by a small amount to correspondingly increase the confidence level necessary to detect the endpoint onset. Similarly, if it is found by diagnostic measurements that the analysis technique is belatedly indicating the onset of endpoint, then the upper control limit can be decreased by a small amount to correspondingly decrease the confidence level necessary to detect the endpoint onset.

The nature of this analysis technique, with or without the updating function, is such that for some applications, an unexpected fault in a process parameter, e.g., a fault in the plasma chamber power level, a fault in the reactant gas delivery system, or other such fault, can produce a process condition that incorrectly indicates the onset of a plasma condition of interest, e.g., main plasma etch endpoint. As can be recognized, the use of diagnostic techniques, such as scanning electron microscopy, to verify the correctness of a process condition indication, can be employed to monitor the validity of the technique under various conditions.

The invention provides additional techniques, also based on principal component analysis, that are particularly well-suited for applications that require the ability to credibly distinguish between a plasma process condition of interest and an unexpected plasma process fault occurring as a process is carried out. The additional techniques also provide a high degree of sensitivity to plasma process wavelength channel correlations even in difficult scenarios such as low open area plasma etch processes.

Figure 4:
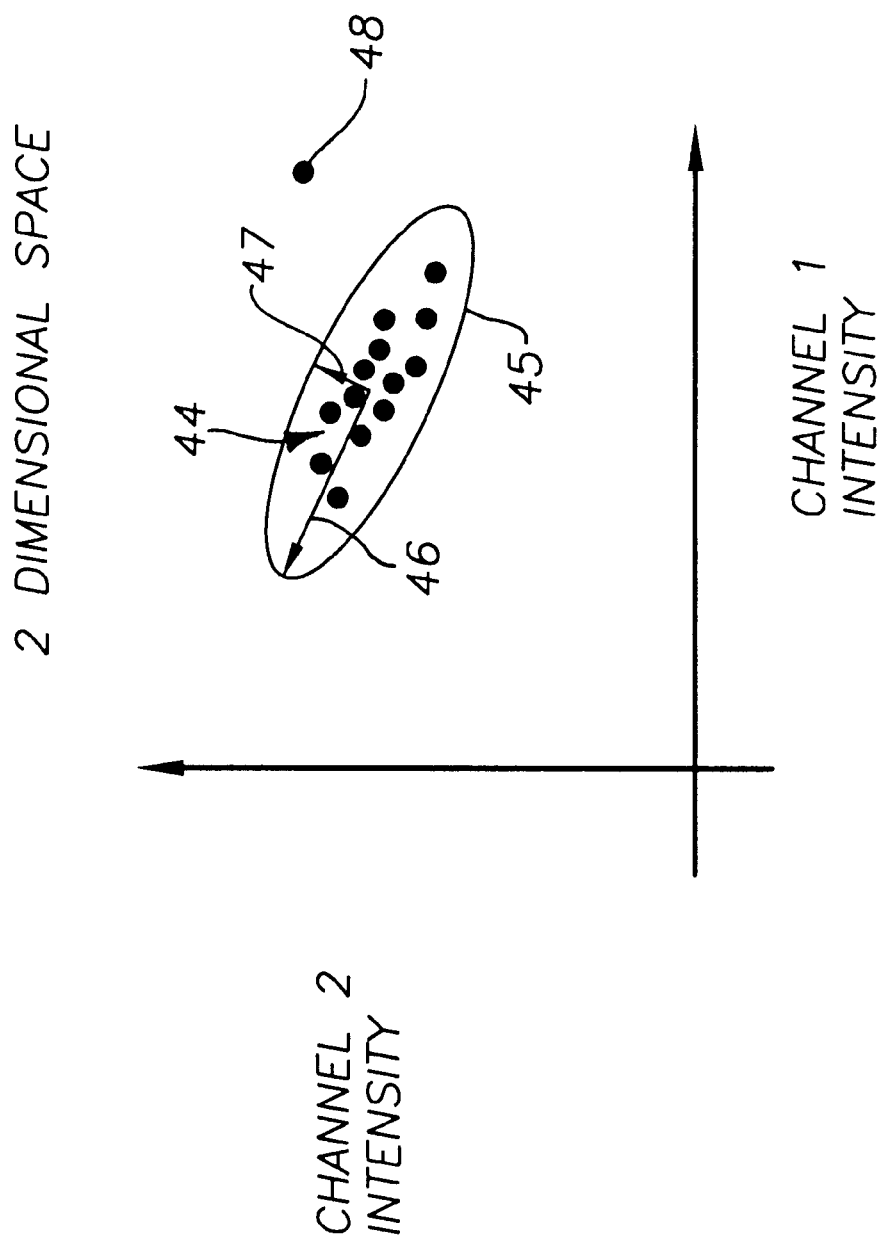
FIG. 4 is an example 2-dimensional emitted wavelength intensity value correlation plot in accordance with the invention for a plasma etch process.

Referring back to FIG. 4, recall that during a steady state plasma process, as the intensity value of each of a number P, of wavelength channels, e.g., two wavelength channels as shown, is monitored over time, the correlation points between the channel intensity values are found to cluster around a local region in P-dimensional space; each point represents the correlation between the channels at a given time. This local correlation region can be characterized by a hyper-ellipsoid in a P-dimensional plot of the correlations. In the nomenclature of principal component analysis, the hyper-ellipsoid is characterized by a corresponding number, P, of principal components, which represent the orthogonal components of the variance in the correlations relative to each channel. In FIG. 4, the first principal component 46 and the second principal component 47 are shown.

Each principal component is characterized by an eigenvector, also called the direction or loading of the component, and a corresponding eigenvalue. The two principal components illustrated in FIG. 4 were given a selected ordering, as just mentioned above, to reflect their relative eigenvalues; component 46 has a larger eigenvalue than component 47 and thus is the first principal component of the two. Following conventional principal component nomenclature, the P principal components for a P-dimensional hyper-ellipsoid are ordered in a descending manner based on their relative eigenvalues. With such an ordering, the component associated with the largest eigenvalue is known to indicate the direction of the maximum variance in the correlation data, and so on, down to the component known to indicate the direction of the minimum variance in the correlation data.

In the additional plasma process analysis techniques provided by the invention, the characteristic hyper-ellipsoid and corresponding principal component eigenvectors and eigenvalues for the hyper-ellipsoid are produced for a selected plasma process condition of interest based on historical process data. Then during analysis of a plasma process to detect the onset of the selected process condition, the eigenvectors of the process under analysis are compared to the historical eigenvectors to determine if the process condition has been reached.

This technique is based on a recognition that for a change in process conditions during a plasma process, the hyper-ellipsoid representing wavelength channel correlations is found to change its orientation and size to encompass additional correlation points that fall outside a previous orientation. The new orientation is an adaptation of the previous orientation that accommodates the new wavelength channel correlations resulting from the process change. Thus, a distinct process condition, such as main plasma etch endpoint, has a corresponding hyper-ellipsoid orientation and size that can be distinguished from other orientations and sizes, such as that found to be characteristic for the steady state of the main etch stage. The set of principal component eigenvectors and eigenvalues for the endpoint condition hyper-ellipsoid thereby represent a distinct correlation relationship that can be exploited for detecting changes in process conditions that correspond to the relationship.

It is the use of both eigenvectors and eigenvalues that renders this detection technique particularly sensitive; both the size and the orientation of a hyper-ellipsoid under examination are considered. Even if a process condition results in only a change in hyper-ellipsoid orientation but no substantial change in hyper-ellipsoid size, the technique can detect such a change. As a result, minor condition changes can be detected. Also, the characteristic eigenvector and eigenvalue relationships, or signature, for a given process condition is of a level of specificity that renders the signature very condition-specific. Unexpected process faults or other conditions aside from a selected process condition can therefore be distinguished to a high degree.

In accordance with the invention, the eigenvector signature, or loading signature, characteristic of the steady state of a plasma process to be analyzed, is produced based on historical wavelength channel intensity data, and the loading signature characteristic of a process condition to be detected is also produced for the data. Then, during monitoring of a process, the loading signature of the process is computed and compared in real time with the loading signature of the process condition of interest, as well as the loading signature of the steady state condition, to determine if the process condition of interest has been reached.

Figure 18:
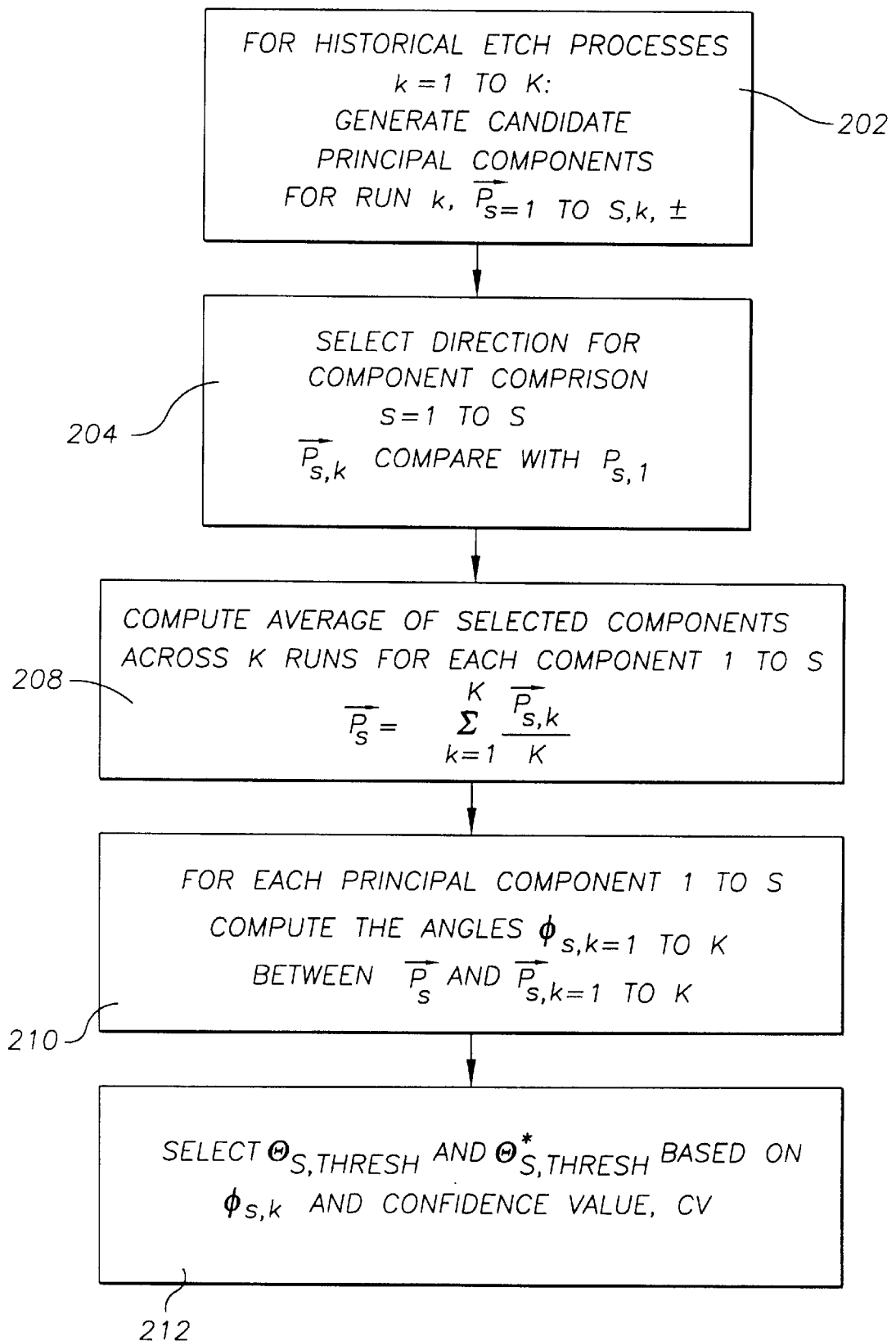
FIG. 18 is a flow diagram of a second example technique for producing historical wavelength correlation indications to be employed in a plasma process monitoring technique provided by the invention.
Figure 19A:
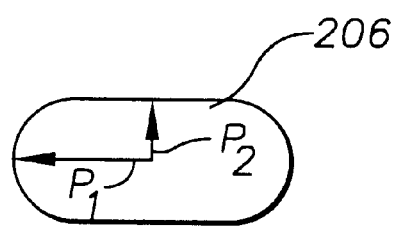
FIGS. 19A–19D are schematic diagrams illustrating four possible principal component orientations that are analyzed by the technique of FIG. 18.
Figure 19B:
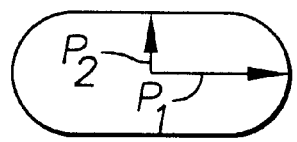
Figure 19C:
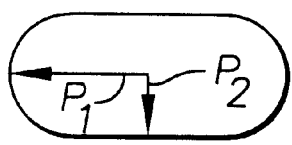
Figure 19D:
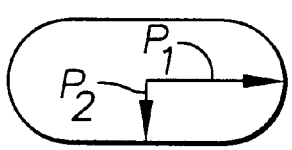

Referring to FIG. 18, this technique is presented for the example scenario of a monitoring analysis to detect the onset of the endpoint of a main plasma etch stage. In a first phase 200 of the analysis, the loading signature of the steady state portion of the main etch stage is produced. For a selected number, K, of historical main etch stage processes to be analyzed, a number, S, of candidate principal components, $\vec{P}_{S,k,\pm}$, are produced and selected 202 for each run, k, in the series of K processes undertaken, for a time period during each of the processes corresponding to the steady state portion of the main etch stage. Then the directionality, or orientation, for each of the S principal component eigenvectors in each of the K processes is selected as described below.

Referring to FIGS. 19A–19D, it is shown that for an ellipsoid 206 in a 2-dimensional plot, there are four possible vector orientation pairings for the two principal component eigenvectors of the ellipsoid. The first principal component vector, $\vec{P}_1$, can be right- or left-oriented, corresponding to a positive or negative direction, respectively, and the second principal component vector, $\vec{P}_2$, can be up- or down-oriented, also corresponding to a positive or negative direction, respectively. In the analysis step 204 of FIG. 18, in making a determination of which vector orientation for each of the selected S principal components being analyzed is to be used, the orientation of each of the selected S principal components that is found for the first historical run, i.e., k=1, is used as a standard. Other of the historical runs could likewise be used as the standard. The dot product between each of the principal components, s=1 to S, of the first run and the corresponding candidate components, $\vec{P}_{s,k,\pm}$, of each of the succeeding runs is then computed. If the absolute value of the resulting dot product angle is less than 90° for a given component, then the candidate component orientation is maintained; otherwise, the opposite sign orientation is imposed on the given component eigenvector orientation. This requirement is based on an expectation that over the sequence of historical runs, a given principal component eigenvector is likely to be oriented in the same angle quadrant for each of the runs, given that the same process is carried out for each of the runs.

Referring back to FIG. 18, with the eigenvector orientations selected, the average principal component signature, $\vec{P}_s$, is then computed 208 taking into account the sequence of K historical runs, for each of the S selected principal components. In other words, an average principal component is produced for each of the S principal components. Next, the difference in orientation between each average principal component, $\vec{P}_s$, and the corresponding s principal component for each of the K historical runs is computed 210. Specifically, the angle, $\phi_{s,k}$, between the average principal component, $\vec{P}_s$, for the principal component s and the s principal component for historical run k is computed as:

$$\phi_{s,k} = \cos^{-1} \vec{P}_{s,k} \cdot \vec{P}_s. \tag{8}$$

Then with this historical orientation data, the main etch threshold eigenvector orientation angle signature, $\Theta_{S,THRESH}$ is selected 212, as explained below, based on a selected confidence value, to be used during monitoring of a main plasma etch stage for the onset of the endpoint condition.

The same steps of this procedure 200 given in FIG. 18 for producing the orientation angle signature for the steady state portion of the main etch stage are also applied in accordance with the invention to a time period during each of the K historical etch processes that is known to include the time at which the main plasma etch stage endpoint condition begins. Following the same steps described above, an endpoint threshold eigenvector orientation angle signature, $\Theta^*_{S,THRESL}$, is selected in step 212, as explained in detail below, to be used with the main etch threshold eigenvector orientation angle signature, $\Theta_{S,THRESH}$ during monitoring of a main plasma etch stage for the onset of the endpoint condition.

Figure 20:
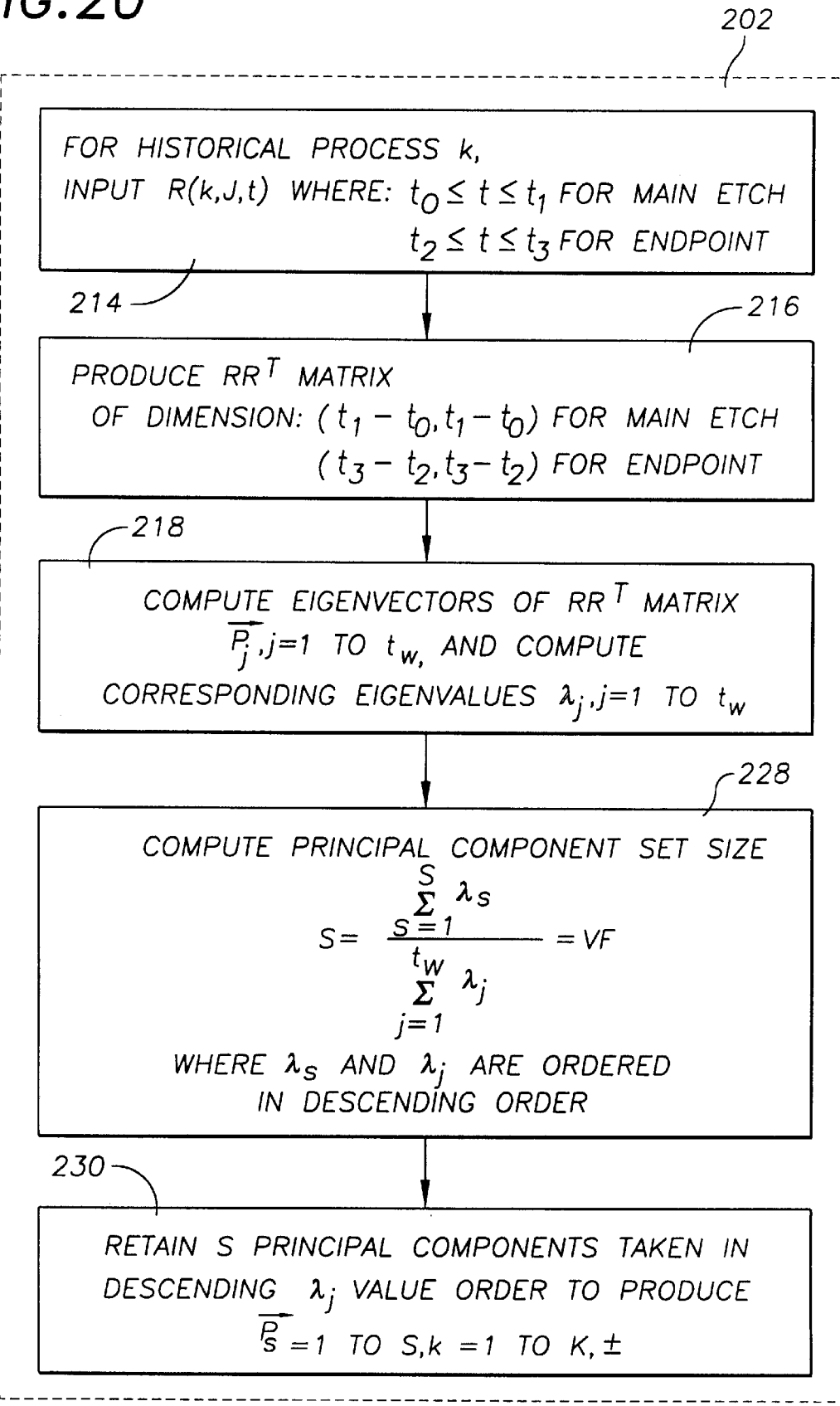
FIG. 20 is a flow diagram of the steps for carrying out the step in FIG. 18 of producing candidate historical principal components.

Turning to details of the procedure of FIG. 18, the step 202 of producing selected candidate principal components for a selected number, S, of components over a sequence of K historical process runs is accomplished following the flow diagram of FIG. 20. First, for each historical process, k, in the sequence of K processes, wavelength channel intensity data, R(k, J, t) is collected 214 for that process and stored using the system configuration of FIG. 1 for a number, J, of wavelength channels. As explained above, if a commercial radiation emission processor, including, e.g., an optical emission spectrometer, is employed, the processor may limit the number of wavelength channels which are available for analysis. In general a larger number of wavelength channels is preferred over a smaller number of wavelength channels.

For producing the main etch stage signature, the wavelength intensity data during a window of time between an analysis start time, $t_0$, and an analysis end time, $t_1$, is selected such that the entire window of time is known to occur during the steady state portion of the main etch stage. For producing the endpoint onset signature, an analysis window of time between a second start time, $t_2$, and a second end time, $t_3$, is selected to include the known time at which endpoint occurs for the main etch stage. Preferably, the start and end times for this endpoint window are selected such that the known endpoint time is at the midpoint of the window of time.

The wavelength channel intensity data collected for historical process k is formatted as a first matrix, $R(k, J, t_0-t_1)$ for the main etch stage and as a second matrix $R k, J, t_2-t_3)$ for the endpoint stage. Each matrix has a number of columns, J, equal to the number of wavelength channels employed, and has a number of rows equal to the number of data sample times; in the case of the main etch stage, equal to the number of data sample times during the $t_1-t_0$ window of time, and in the case of the endpoint stage, equal to the number of data sample times during the $t_3-t_2$ window of time. As can be recognized, the data sampling is spaced to produce a desired speed of detection, as explained above. As shown in FIG. 20, the matrix computation $R(k, J, t)R^T(k, J, t)$ is then carried out 216 separately for the main etch stage and endpoint stage matrices, where the superscript T indicates transposition. Each resulting covariance matrix has an equal number of rows and columns, equal to the number of time samples in the analysis time window, $t_w$, under consideration. Because the number of time samples in an analysis window is likely to be less than the number of wavelength channels employed, this computation reduces the processing requirements of the succeeding steps and enhances the overall speed of the analysis technique.

Figure 21:
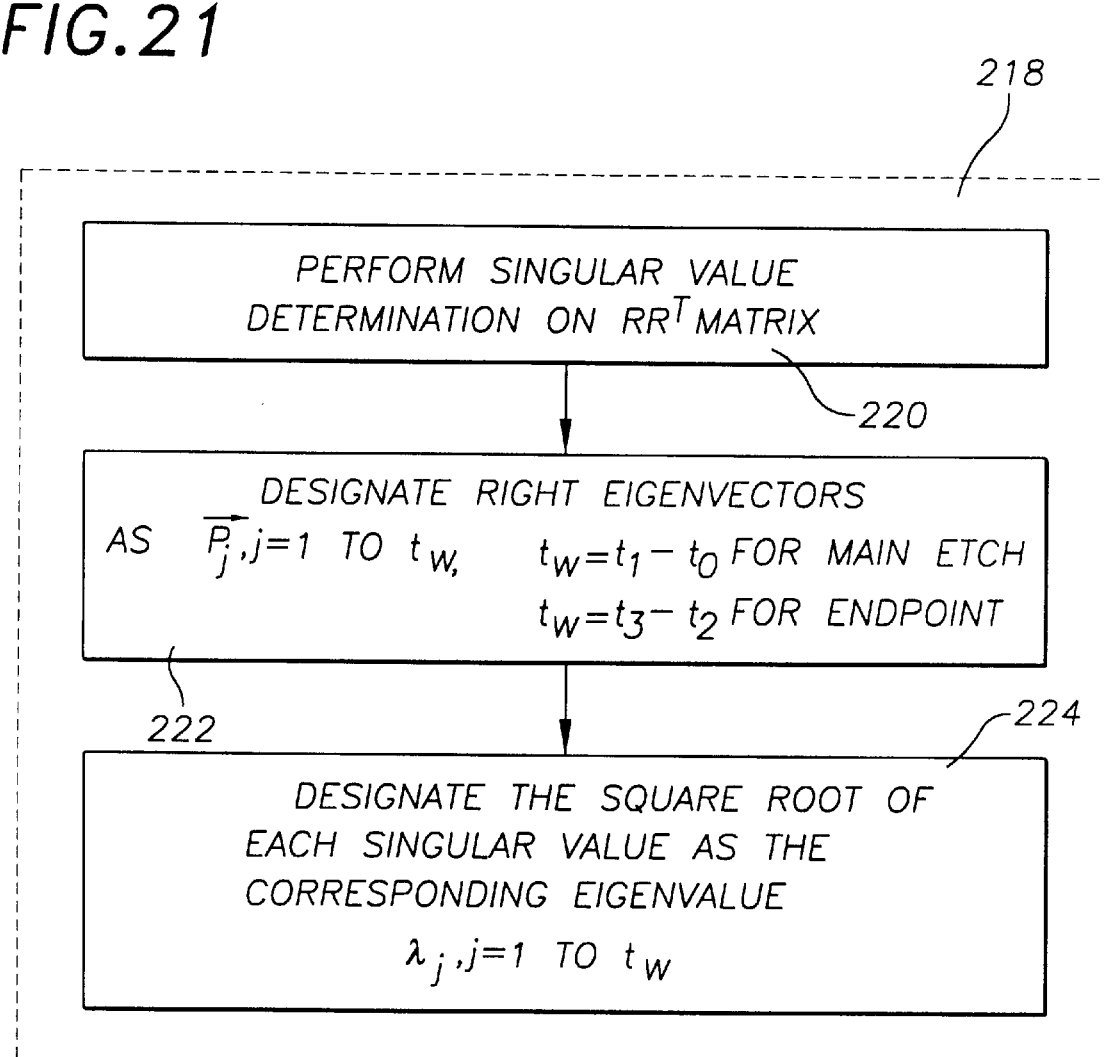
FIG. 21 is a flow diagram of the steps for carrying out the step in FIG. 20 of computing historical eigenvectors and eigenvalues.

In the next step toward production of the main etch and endpoint stage signatures, the eigenvectors and corresponding eigenvalues of each $RR^T$ matrix are computed 218. Turning to the flow diagram of FIG. 21, in this process 218, singular value decomposition (SVD) or other suitable eigenvalue/eigenvector matrix decomposition technique is performed 220 on each matrix. A conventional SVD or other decomposition computation implementation can be employed, e.g., the computation implementation provided by the MATLAB software processing environment specified above. The right eigenvectors, $\vec{P}_{j=1-t_w}$, from the computation are then designated 222 for each matrix, corresponding to the J wavelength channels for the time window, $t_w$ being analyzed. In other words, each time sample in the time window enables computation of an additional principal component eigenvector capturing correlation among the J wavelength channels being analyzed. The square root of the singular values produced by the SVD step 220 for each matrix are then designated 224 as the corresponding eigenvalues, $\lambda_{j=1-t_w}$, for the J wavelength channels for the time window, $t_w$, being analyzed.

Turning back to the flow diagram of FIG. 20, with the eigenvectors and eigenvalues computed 218, next the principal component set size designating the number, S, of principal components to be retained out of the J available principal components is computed 228. To make this computation, the eigenvalues for the main etch stage matrix are ordered in descending order along with the corresponding eigenvectors, and the eigenvalues for the endpoint stage matrix are ordered in descending order along with the corresponding eigenvectors. Then the number, S, of components to be retained for each of the stages is determined based on the following relationship:

$$S = \frac{\sum_{s=1}^{S} \lambda_s}{\sum_{j=1}^{t_w} \lambda_j} = VF = 0.98; \tag{9}$$

where an example variance factor, VF, of 0.98 has been employed. The variance factor is set to a selected value corresponding to a percentage of variance in the $RR^T$ covariance matrix that is desired to be captured by the selected set of principal components. For example, a VF of 0.98 imposes a criterion that the selected set of principal components capture 98% of the variance in the $RR^T$ matrix; a relatively larger VF results in a wider spread of principal component correlation variation, while a relatively smaller VF results in a more narrow spread in principal component correlation variation. In carrying out the computation for this relationship (9), the summation factors are evaluated over the descending order sets of eigenvalues.

The value of S that provides the selected variance factor in relationship (9) is then used in a next step 230 to retain the first number, S, of principal components, taken in descending $\lambda_j$ value order, for use in computing the main etch stage threshold eigenvector orientation angle signature, $\Theta_{S,THRESH}$, and the endpoint threshold eigenvector orientation angle signature, $\Theta^*_{S,THRESH}$, as given in the threshold setting step 212 given above. Preferably, the variance factor relationship (9) above is carried out for the main etch eigenvalue set and the endpoint eigenvalue set and then the S values from the two relationships are compared; the lower of the two S values is then selected to be imposed on both the main etch eigenvalue set and the endpoint eigenvalue set. Then the set of S principal components is designated for the main etch stage and the set of S principal components is designated for the endpoint stage, both for each of the K historical etch processes.

Then going back to the procedure 200 of FIG. 18, the direction of each of the principal component eigenvectors for each of the historical etch processes is selected by comparison 204 with the principal component eigenvector orientations of the first historical etch process. The procedure then continues as described above, with the average for each principal component computed 208 across the K processes, and the angle between each principal component eigenvector and the corresponding average eigenvector then computed 210. Finally, the main etch stage threshold eigenvector orientation angle signature, $\Theta_{S,THRESH}$, and the endpoint threshold eigenvector orientation angle signature, $\Theta^*_{S,THRESH}$, are selected.

Figure 22:
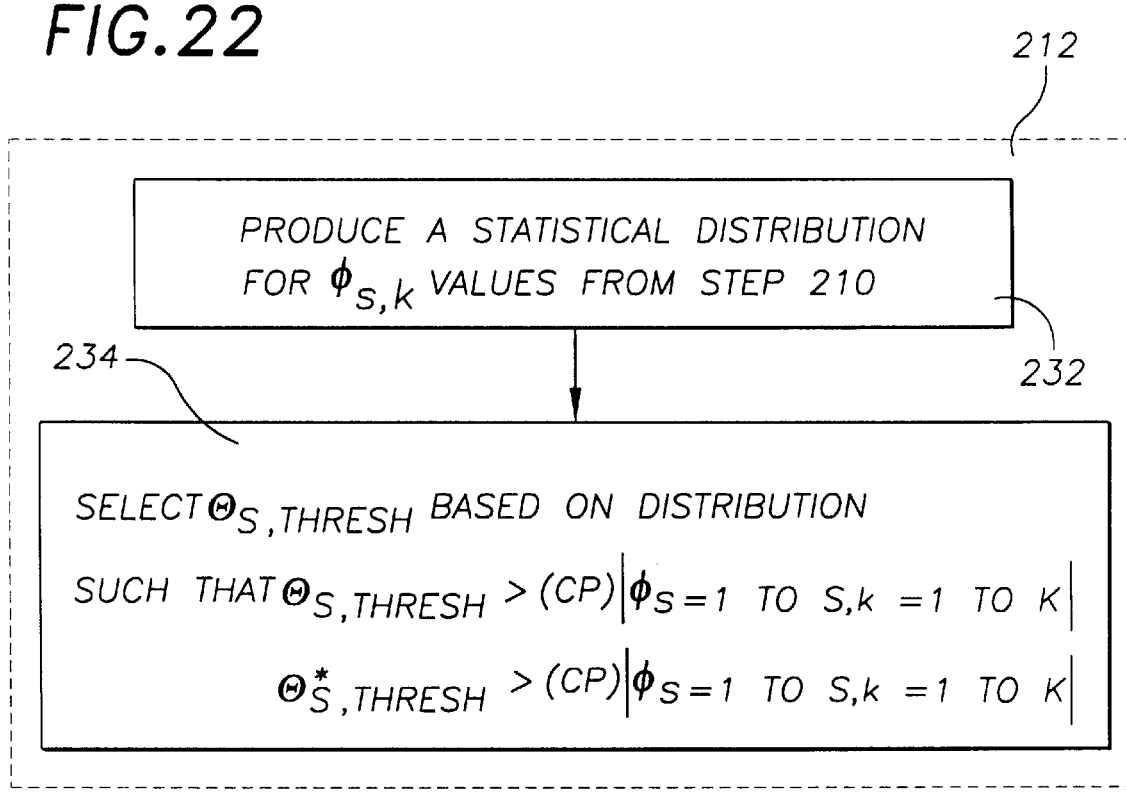
FIG. 22 is a flow diagram of the steps for carrying out the step in FIG. 18 of selecting threshold eigenvector orientation angles.

Referring to FIG. 22, in the process for selecting the threshold signatures, the statistical distribution for the computed angles between the eigenvector of the principal components and the eigenvectors of the corresponding average principal components is produced 232. Then the threshold angle is selected 234 such that the threshold angle is greater than a confidence percentage CP, of the computed angles. Accordingly, the main etch stage threshold eigenvector orientation angle signature, $\Theta_{S,THRESH}$, is selected to be greater than the selected confidence percentage, CP, of the computed angles for the S principal components from the main etch set of principal components, and the endpoint threshold eigenvector orientation angle signature, $\Theta^*_{S,THRESH}$, is selected to be greater than the selected confidence percentage, CP, of the computed angles for the S principal components form the endpoint set of principal components.

It is found that the distribution of principal component eigenvector angles over the historical etch processes is typically a Gaussian distribution, whereby a symmetric limit on the distribution can be employed using a standard statistical plot of the computed eigenvector angles. A confidence percentage, CP, of 99%, e.g., will then capture 99% of the eigenvector angles over the K etch processes. The confidence percentage for establishing $\Theta_{S,THRESH}$ corresponds to the frequency of endpoint detection for a set of main etch stage eigenvector angle values; for example, a confidence percentage of 99% imposes a condition in which endpoint will be detected for one out of 100 main etch stage eigenvector angle values. Thus, a relatively higher confidence percentage decreases the sensitivity of the detection process, but as can be recognized, also decreases the potential for false endpoint detection.

Figure 23:
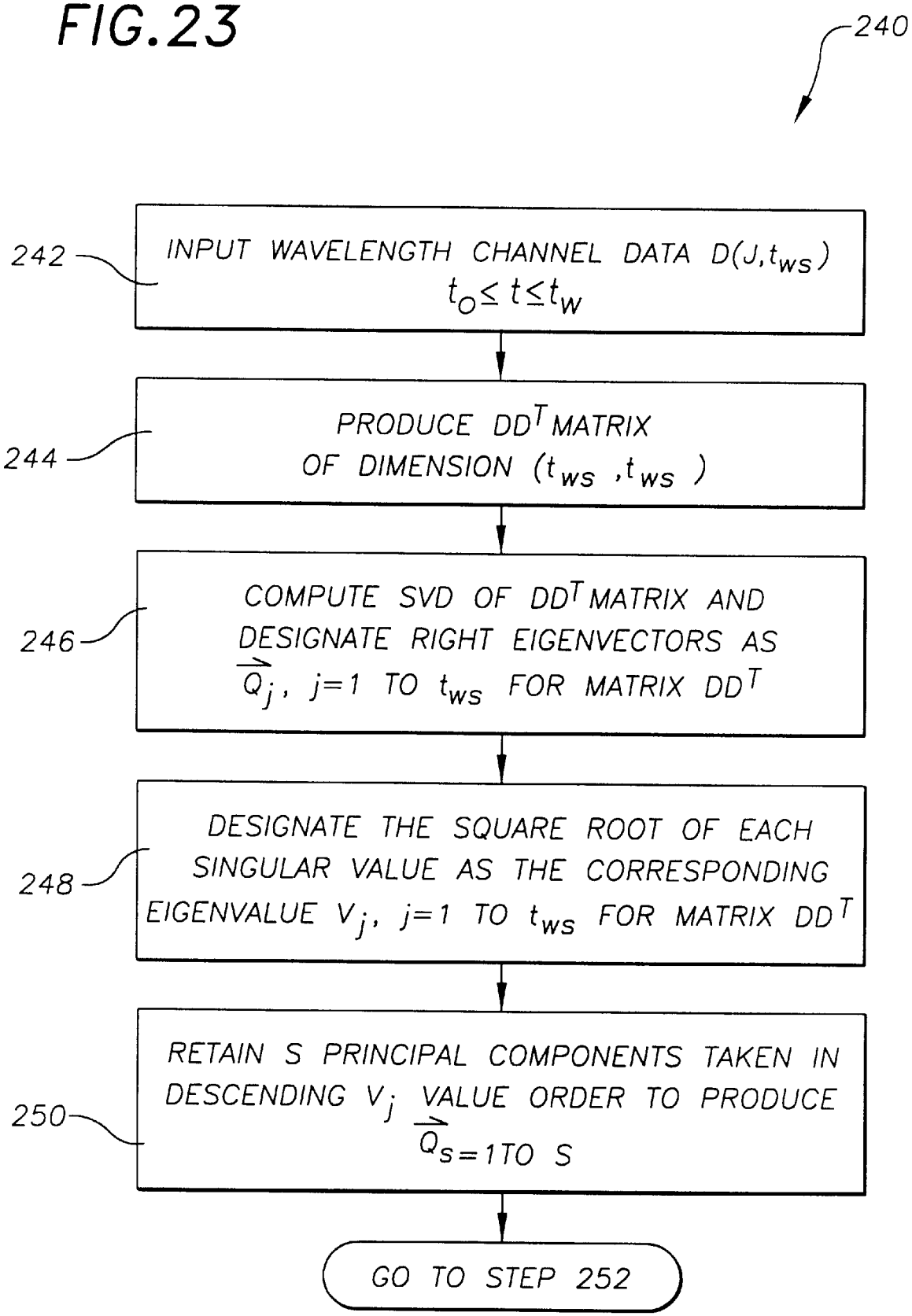
FIG. 23 is a flow diagram of an example plasma process monitoring technique employing the historical wavelength correlation indications produced by the flow diagram steps of FIG. 18.

With the main etch stage threshold eigenvector orientation angle signature, $\Theta_{S,THRESH}$, and the endpoint threshold eigenvector orientation angle signature, $\Theta^*_{S,THRESH}$, selected, real-time monitoring of a process for the endpoint condition can be carried out. Referring to FIG. 23, in the process 240 for detecting endpoint of a main plasma etch stage, wavelength channel intensity data, D(J, t), is measured and collected using the system arrangement of FIG. 1, for the selected number, J, of wavelength channels, and over the time, t, that corresponds to window of time during the etch currently being monitored.

In a first scenario in accordance with the invention, wavelength channel data is collected from a first time, $t_0$, designating the start of the time window under consideration, until a later time, $t_w$, designating the end of the time window under consideration. The wavelength channel data is stored as the etch proceeds through the given time window until the current time coincides with the time window end, $t_w$. The size of the time window during which wavelength channel data is collected can be selected to achieve a desired analysis sensitivity, and does not need to coincide with the window size that was imposed on the historical channel data. Specifically, for some applications, it may be preferably to set the real-time wavelength channel collection window size smaller than the historical window size to minimize the delay introduced while the window is completely traversed prior to the start of the analysis. In the limiting case the time window can be specified to include only one time sample of wavelength channel data. This extreme adaptation may not be preferable for most applications, as it may be susceptible to false endpoint detection. A more robust analysis window of time, including, e.g., at least about four real-time wavelength channel data sample, is preferred.

In an alternative scenario, as the etch proceeds, the real-time analysis described below can be carried each time a new time sample of wavelength channel data is added to the growing collection of data. Once a specified window of time is reached, a final analysis can be completed, after which a new collection of data is begun based on an adjusted time window.

Considering an example scenario in which the analysis is carried out after a complete window of data is collected, the collected data is formatted 242 as a data matrix D(J, $t_{ws}$) having a number of columns, J, corresponding to the number of wavelength channels, and a number of rows, $t_{ws}$, corresponding to the number of time samples of intensity values that were collected for the window of time under consideration. The covariance matrix is then produced 244 as $DD^T$, where the superscript T indicates transposition. The $DD^T$ covariance matrix is of equal number of columns and rows, both being equal to the number of time samples in the time window under consideration. Using singular value decomposition (SVD) or other suitable technique, the right eigenvectors, $\vec{Q}_j$, where j=1 to $t_{ws}$, for the covariance matrix are computed 246. The square root of each singular value computed is then designated 248 as the corresponding eigenvalue, $V_j$, where j=1 to $t_{ws}$. Thereby a number, $t_{ws}$, of principal components $\vec{Q}_{j=1-t_{ws}}$, with a number, $t_{ws}$, of corresponding eigenvalues, $V_{j=1-t_{ws}}$, are produced.

The value of the principal component set number, S, selected during the historical data analysis phase at step 228, is then imposed on the set of $t_{ws}$ principal components here, ordered in descending value of the eigenvalues. As a result, a set of S principal components $\vec{Q}_s$ having the relatively largest eigenvalues, is retained 250 for further analysis to detect the onset of the endpoint condition during the time window under consideration.

Figure 24:
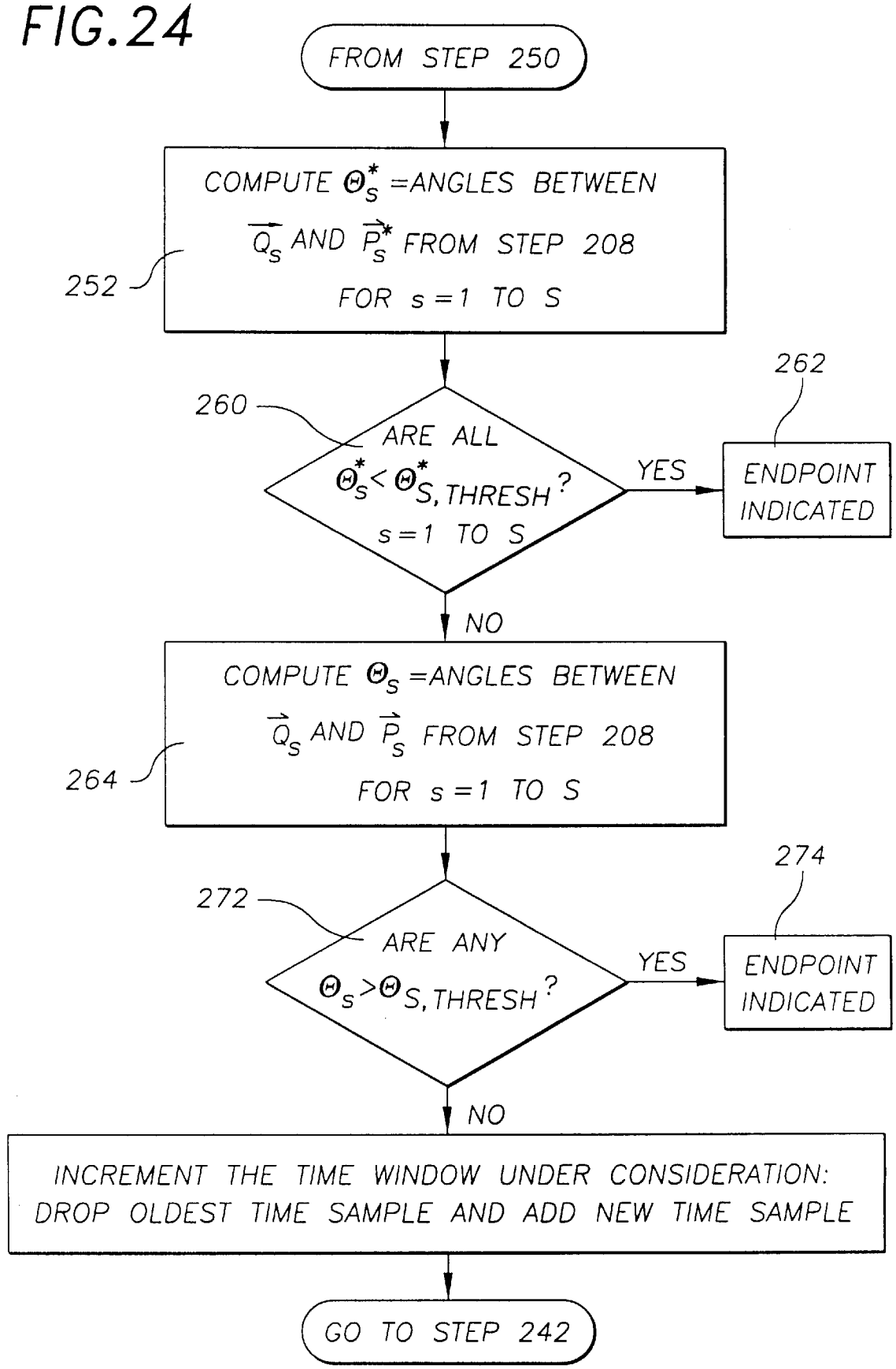
FIG. 24 is a continuation of the flow diagram of FIG. 23.
Figure 25:
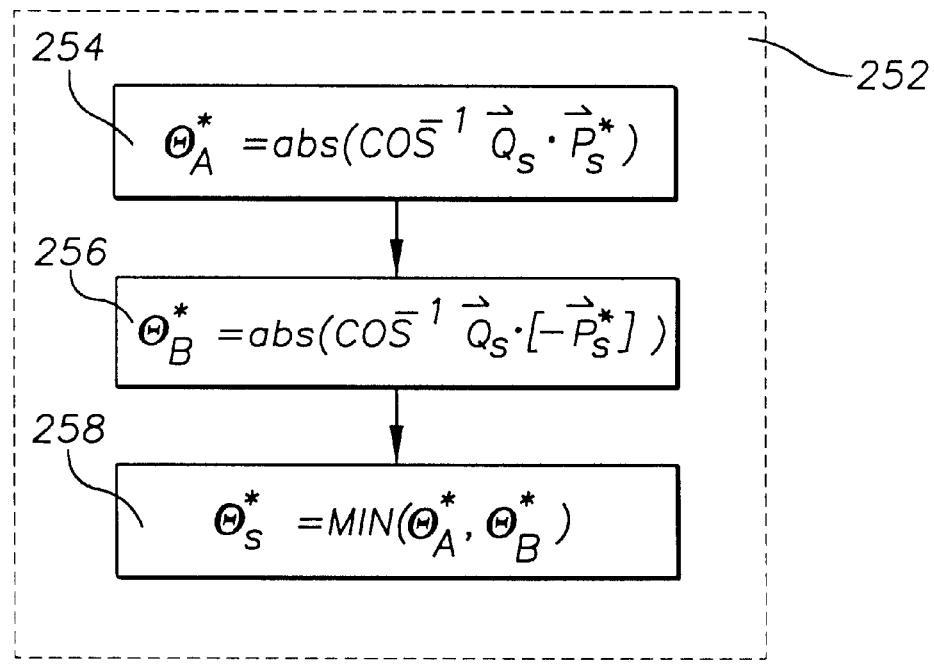
FIG. 25 is a flow diagram of the steps for carrying out the step in FIG. 24 of computing eigenvector orientation angles for an endpoint signature.

Continuing with step 252 of the procedure in FIG. 24, the angle between each of the S eigenvectors of the $\vec{Q}_s$ principal components from the collected data and the average corresponding principal component $\vec{P}_s$ taken from the set of endpoint stage principal components produced in step 208 is computed. Referring also to FIG. 25, in this computation 252, a first eigenvector angle, $\Theta^*_A$, is computed 254 for the $s^{th}$ principal component as:

$$\Theta^*_A = \text{abs}(\cos^{-1} \vec{Q}_s \cdot \vec{P}^*_s). \tag{10}$$

A second eigenvector angle, $\Theta_B$, is similarly computed 256 for the $s^{th}$ principal component as:

$$\Theta^*_B = \text{abs}(\cos^{-1} \vec{Q}_s \cdot [-\vec{P}^*_s]). \tag{11}$$

These two relationships capture the two possible orientation pairings between the eigenvector of each endpoint stage average principal component and the eigenvector of the corresponding principal component from the collected data. In the next succeeding step, the characteristic endpoint eigenvector angle $\Theta^*_s$ for the $s^{th}$ principal component is then selected 258 from the $\Theta^*_A$ and $\Theta^*_B$ values as:

$$\Theta^*_s = \min(\Theta^*_A, \Theta^*_B). \tag{12}$$

This condition is based on the assumption explained above that the eigenvectors for a given principal component can be expected to fall in a common half-plane of angles; the selection of the minimum angle in this relationship (12) results in an angle that is most likely to correspond to this assumption.

Referring back to FIG. 24, after the S endpoint eigenvector angles, $\Theta^*_s$, have been computed, it is determined 260 if each of the computed eigenvector angles, $\Theta^*_s$, is less than the endpoint threshold eigenvector orientation angle signature, $\Theta^*_{S,THRESH}$, produced in step 212. If every one of the eigenvector angles meets the requirement, then it is definitively known that the hyper-ellipsoid characteristic of the current time window under consideration falls within the orientation and value signatures for the historical endpoint stage hyper-ellipsoid, and accordingly, the onset of the endpoint condition is indicated 262.

Figure 26:
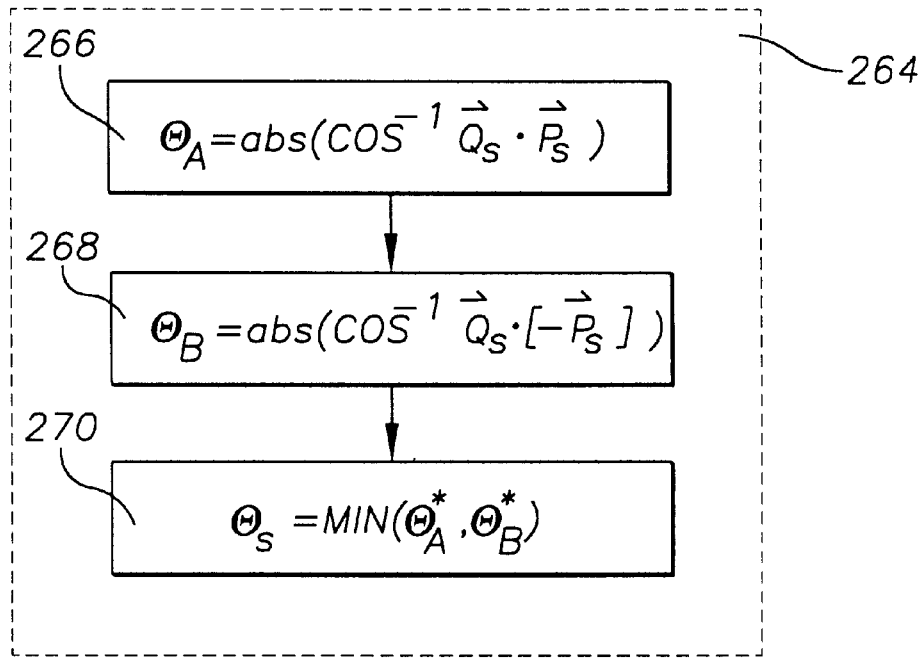
FIG. 26 is a flow diagram of the steps for carrying out the step in FIG. 24 of computing eigenvector orientation angles for a main etch signature.

If at least one of the computed eigenvector angles, $\Theta^*_s$, does not meet the requirement, then an additional eigenvector angle analysis is carried out. Here, the angle between each of the S eigenvectors of the $\vec{Q}_s$ principal components from the collected data and the average corresponding principal component $\vec{P}_s$, taken from the set of main etch stage principal components produced in step 208 is computed 264. Referring also to FIG. 26, in this computation 264, a first eigenvector angle, $\Theta_A$, is computed 266 for the $s^{th}$ principal component as:

$$\Theta_A = \text{abs}(\cos^{-1} \vec{Q}_s \cdot \vec{P}_s), \tag{13}$$

and a second eigenvector angle, $\Theta^*_B$, is similarly computed 268 for the $s^{th}$ principal component as:

$$\Theta_B = \text{abs}(\cos^{-1} \vec{Q}_s \cdot [-\vec{P}_s]). \tag{14}$$

These two relationships capture the two possible orientation pairings between the eigenvector of each endpoint stage average principal component and the eigenvector of the corresponding principal component from the collected data. In the next succeeding step, the characteristic main etch stage eigenvector angle, $\Theta_s$, for the $s^{th}$ principal component is then selected 270 from the $\Theta_A$ and $\Theta_B$ values as:

$$\Theta = \min(\Theta_A, \Theta_B). \tag{15}$$

Then, referring back to FIG. 24, it is determined 272 if any of the computed main etch stage eigenvector angles, $\Theta_s$, are larger than the main etch stage threshold eigenvector orientation angle signature, $\Theta_{S,THRESH}$, produced in step 212. If any of the principal component eigenvector angles do not meet the criterion, then it is known that the hyper-ellipsoid characteristic of the time window under consideration does not fall within the orientation and value signatures for the hyper-ellipsoid of the main etch stage for the historical data. As a result, it is indicated 274 that the onset of the endpoint condition has been reached. This indication step is a conservative fall-back step that catches those endpoint conditions which are not correctly identified by the endpoint stage threshold eigenvector orientation angle signature determination in step 260. The indication of endpoint at this step or at the previous indication step 262 in the process can be signaled, as described above, to control systems for the etch chamber, to correspondingly control the etch chamber conditions for, e.g., halting the main etch parameters.

If it is found that none of the computed main etch stage eigenvector angles, $\Theta_s$, are larger than the main etch stage threshold eigenvector orientation angle signature, $\Theta_{S,THRSH}$, produced in step 212, then no onset of the endpoint condition is indicated and the time window under consideration is incremented 276 to move one time sample forward in the etch process being monitored. Accordingly, the oldest time sample is dropped from the wavelength channel intensity data stored during the last window and the next time sample, corresponding to a forward step in time through the etch process, is added to the window. With this adjustment of the window "frame" along the flow of the etch process, the real time analysis is carried out on the time samples that fall within the new window, starting again at the procedure step 242.

The invention contemplates a range of adaptations of this analysis technique. For example, when the wavelength channel data is collected during the historical data analysis phase at step 214, and when the wavelength channel data is collected during a current time window in a process being monitored at step 242, the intensity values of the wavelength channel data can be filtered to remove those channels having an intensity value less than some minimum value. This filtering step reduces the initial data matrix column size. It is noted, however, that the step of ordering the computed principal components prior to selecting the value S of the principal component set size to be retained has an inherent filtering action, and so for many applications, a specific filtering step may not be warranted.

In addition, prior to the step 218 of computing the principal components for the historical data and prior to the step 246 of computing the principal components for a process being monitored, the data matrices can be mean-centered. With such a centering function included, the eigenvector orientation angle analyses in the procedure detect differences in eigenvector orientation from the mean eigenvector orientation for a given component.

In a further adaptation, the steps 210, 212 of computing the eigenvector angle between a given principal component and average for that component can be adjusted, along with the step of correspondingly selecting a threshold eigenvector orientation angle. Specifically, the threshold for eigenvector orientation angle can be computed based on confidence intervals for empirical distributions generated from all possible orientation angles, between all pairs of corresponding eigenvectors from historical data. For example, four historical runs can be carried out to generate four first principal component eigenvectors for a main etch stage. Six pairings of these four vectors can be produced, e.g., runs one and two, runs three and four, and so on, with a pair angle computed for each of the pairings. It is seen that a large distribution of empirical eigenvector pairing angles can be generated with a relatively small number of historical runs. A confidence limit, e.g., a 95% confidence limit, on acceptable or "usual" angles can then be established and used to set a threshold limit to detect an "unusual" angle.

In other adaptations, an exponentially-weighted moving average (EWMA) can be applied to an appropriate variable, e.g., the computed threshold angles, to update the analysis based on drifts in the plasma process conditions, in the manner described above. For example, in the manner previously described, the most recent run can be treated as a new historical run for recomputation of the "average eigenvector directions" $\vec{P}_s$ and $\vec{P}^*_s$ for characteristic main etch and endpoint stages. When computing these averages, at step 208, the most recent runs can be given larger weights compared to earlier runs, so that the resulting threshold values, $\Theta_{S,THRESH}$, $\Theta^*_{S,THRESH}$, can reflect any slow drifts or changes in the processing equipment.

In a further adaptation, historical analysis for producing threshold values, e.g., for producing a $\Theta_{S,THRESH}$ value, can be carried out in real time during a plasma etch being monitored prior to the time of analysis of wavelength channel data during the same process. The invention also contemplates further adaptations in which only one of the historical main etch or end point signature analyses is employed; e.g., an endpoint detection analysis can be carried out where endpoint is indicated if a measured eigenvector angle signature is greater than the historical $\Theta_{S,THRESH}$ value produced for the main etch stage. Similarly, an endpoint detection analysis can be carried out where endpoint is indicated if a measured eigenvector angle signature is less than the historical $\Theta^*_{S,THRESH}$ value produced for the endpoint stage.

As with the Hotelling's $T^2(t)$ analysis technique provided by the invention that was described above, the eigenvector signature analysis technique can be applied to various stages of a plasma etch process and to plasma processes other than etch processes. Whatever the stage or process to be monitored, the principal components for the hyper-ellipsoid that characterizes wavelength channel intensity value correlations for the steady state and for a condition to be detected are produced and analyzed in the manner described for a sequence of historical data collection processes. Then real time monitoring of a process to detect the stage or condition of interest can be undertaken in the same manner. This detection of a process stage or condition of interest can be extended to detection of a fault condition in the process which results in a corresponding shift of the principal component hyper-ellipsoid. Here a fault threshold signature is produced in the manner of the thresholds discussed above and a determination is made as to whether the process being monitored has undergone the fault condition of interest or alternatively, a general, non-specific, fault condition.

Figure 27:
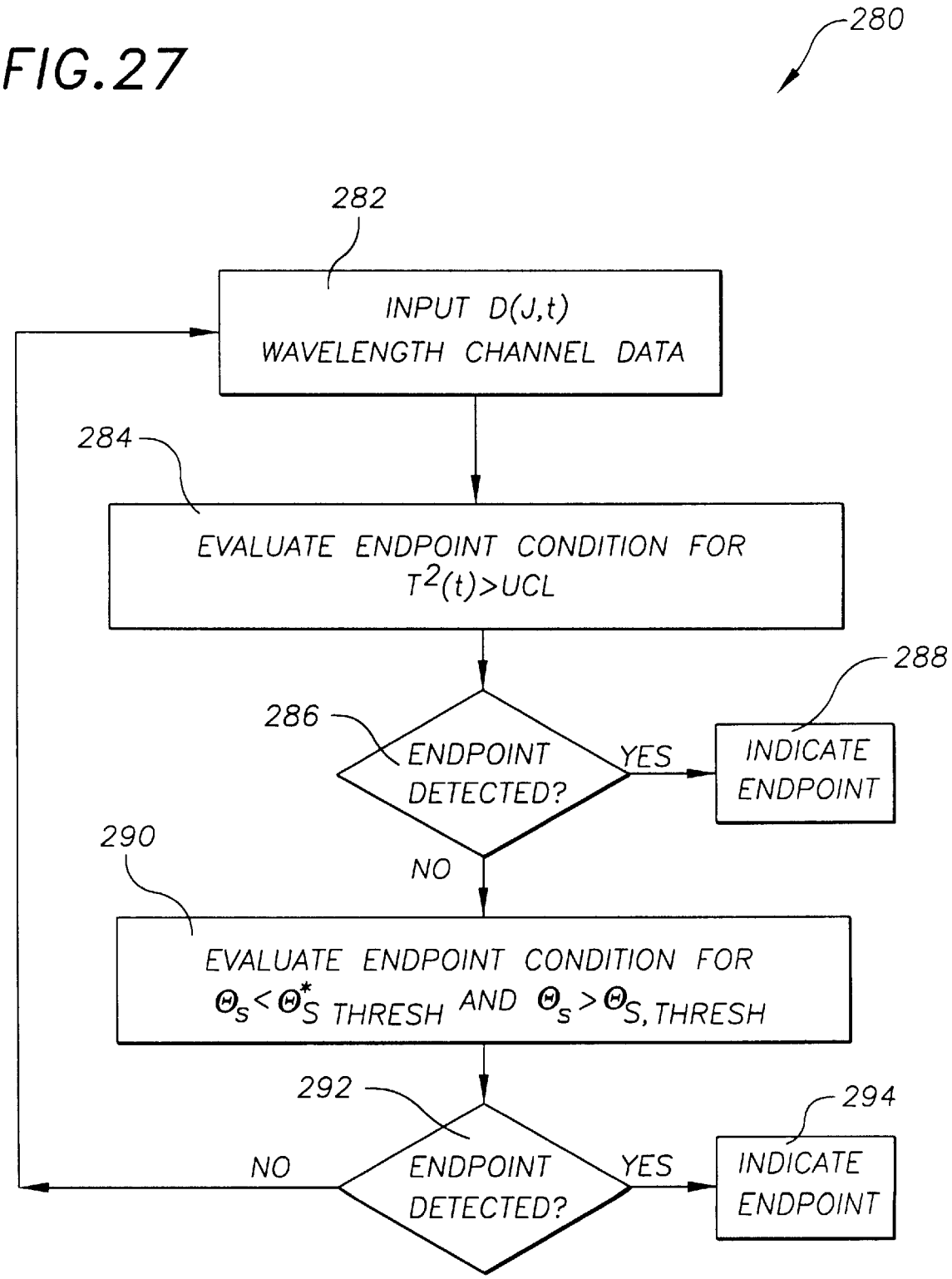
FIG. 27 is a flow diagram of a first example plasma process monitoring technique that combines the techniques of the flow diagrams of FIGS. 9 and 23.

Referring now to FIG. 27, the invention contemplates a dual endpoint detection technique 280 in which the Hotelling's $T^2(t)$ analysis described above is combined with the eigenvector angle orientation analysis just described. In this technique, wavelength channel intensity value data $D(J, t)$, for a number, J, of wavelength channels, is measured and collected 282 for times t within a selected window of time. Then the Hotelling's $T^2(t)$ analysis is carried out 284 for a prespecified $T^2(t)$ function and upper control limit (UCL) value for the most recent time sample of intensity values added. If the onset of the endpoint of the main etch stage under analysis is detected 286 by the $T^2(t)$ analysis, then the onset of endpoint is indicated 288.

If the $T^2(t)$ analysis does not detect endpoint, then the threshold eigenvector angle orientation analysis is carried out 290 for prespecified main etch and endpoint stage threshold angle signatures. If this analysis detects 292 the onset of endpoint, then endpoint is here indicated 294, or else the process is repeated starting at step 282 for the next spectrum of wavelength channel intensity value samples.

Figure 28:
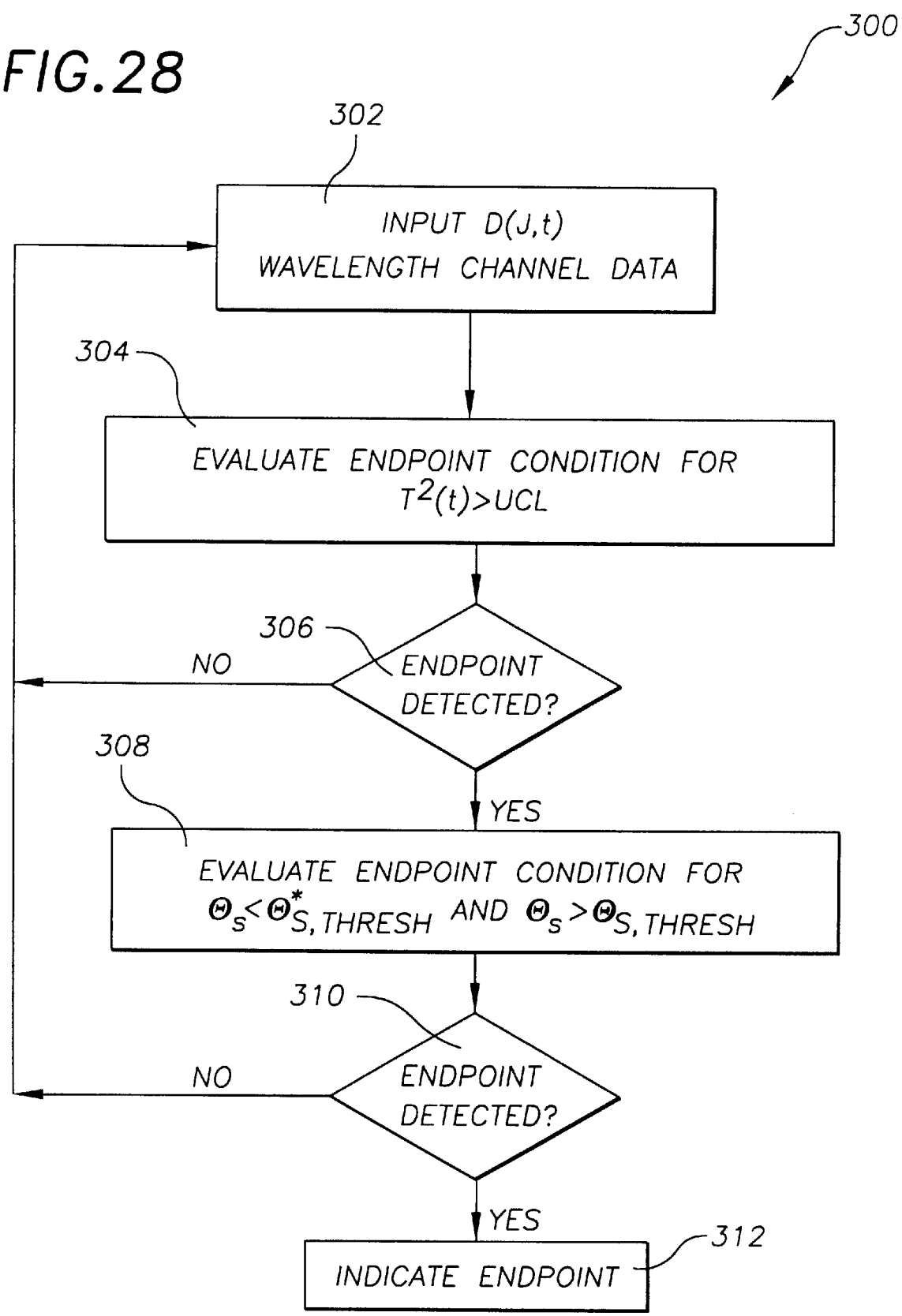
FIG. 28 is a flow diagram of a second example plasma process monitoring technique that combines the techniques of the flow diagrams of FIGS. 9 and 23.

Referring to FIG. 28, in an alternative technique 300 that combines the two analyses, first steps of inputting 302 wavelength channel intensity data and applying 304 the Hotelling's $T^2(t)$ analysis are again carried out. But unlike the previous process, here if the $T^2(t)$ analysis evaluation 306 of endpoint does not detect endpoint, then the analysis process is restarted at step 302 with the next spectrum of wavelength channel intensity value samples.

If the $T^2(t)$ analysis does detect endpoint, then the threshold eigenvector angle orientation analysis is carried out 308. If evaluation 310 of endpoint here does not detect endpoint, then the analysis process is restarted at step 302 with new spectrum data. If the evaluation 310 does detect endpoint, then endpoint is indicated 312. This analysis process 300 is seen to require for indication of a valid endpoint condition the detection of the endpoint condition by both the threshold eigenvector angle orientation analysis and the Hotelling's $T^2(t)$ analysis. The previous process 280 is seen to require for indication of a valid endpoint condition the detection of the endpoint condition by either the threshold eigenvector angle orientation analysis or the Hotelling's $T^2(t)$ analysis. The process 300 requiring dual endpoint detections provides a high degree of robustness, while the process 280 requiring endpoint detection by either of the two analyses provides a high degree of sensitivity.

The above description highlights the many advantages of the plasma process monitoring techniques provided by the invention. The techniques provide a high degree of sensitivity to plasma process conditions, and are robust in that they can operate effectively even under conditions of process fluctuations over the course of a sequence of processes. The techniques are flexible in that they together accommodate various representations of process conditions, and can be adapted for process condition detection with a desired response times and combinations of off-line and real-time processing. The wide range of plasma processes, including plasma etch processes, are found to be particularly well-addressed by the analysis techniques of the invention. It is recognized, of course, that those skilled in the art may make various modifications and additions to the plasma process monitoring techniques described above without departing from the spirit and scope of the present contribution to the art. Accordingly, it is to be understood that the protection sought to be afforded hereby should be deemed to extend to the subject matter of the claims and all equivalents thereof fairly within the scope of the invention.

We claim:

1. A method for monitoring the status condition of a plasma process as the plasma process proceeds, the method comprising the steps of:

monitoring the intensity of each of a number, P, of a plurality of radiation wavelengths that are emitted from the plasma process as the process proceeds;

producing indications of P-dimensional correlations between the intensities of the P monitored wavelengths as the process proceeds; and comparing the produced correlation indications with a prespecified correlation indication generated based on historical conditions for the plasma process, to determine the status condition of the process as the process proceeds.

2. The method of claim 1 wherein the emitted radiation wavelengths that are monitored comprise radiation wavelengths between about 200 nm and about 800 nm.

3. The method of claim 1 wherein the number, P, of monitored radiation wavelengths is at least 2.

4. The method of claim 3 wherein the number, P, of monitored radiation wavelengths is at least about 10.

5. The method of claim 4 wherein the number, P, of monitored radiation wavelengths is at least about 100.

6. The method of claim 5 wherein the number, P, of monitored radiation wavelengths is at least about 500.

7. The method of claim 1 wherein the plasma process for which the status condition is determined is a plasma etch process.

8. The method of claim 7 wherein the plasma process for which the status condition is determined is a main etch stage of a plasma etch process.

9. The method of claim 8 wherein the step of comparing produced correlation indications with a prespecified correlation indication comprises a comparison to determine if a condition of etch endpoint has been reached.

10. The method of claim 9 wherein the plasma process for which the status condition is determined is a plasma etch process employing reactive plasma species for plasma etching oxide.

11. The method of claim 1 further comprising a last step of controlling process parameters of the plasma process in response to the process status condition determination.

12. The method of claim 1 further comprising:

a first step of carrying out a number, K, of historical plasma processes during each of which the intensity of each of the P radiation wavelengths are monitored; and a second step of producing the prespecified correlation indication based on the intensities of the P monitored wavelengths for the process conditions of the K historical processes carried out.

13. The method of claim 1 further comprising a step of producing the prespecified correlation indication during the plasma process prior to the step of comparing the produced correlation indications with the prespecified correlation indication.

14. The method of claim 1 further comprising a step of producing, for each of the monitored intensities of the P radiation wavelengths, a digital intensity value signal to be used for producing the P-dimensional correlation indications as the plasma process proceeds.

15. The method of claim 1 further comprising a step of updating the prespecified correlation indication based on the produced correlation indication.

16. The method of claim 15 wherein the updating step comprises applying an exponentially-weighted moving average, based on historical process condition drift, to the prespecified correlation indication.

17. The method of claim 1 wherein the step of monitoring the intensities of the P radiation wavelengths comprises the steps of:

monitoring the intensity of each of a number, J, of radiation wavelengths, where J>P; and filtering the J monitored wavelength intensities to select those P wavelengths that each meet a prespecified intensity criterion.

18. The method of claim 1 wherein the step of producing indications of the P-dimensional intensity correlations comprises producing P-dimensional intensity correlation values, and wherein the step of comparing the produced correlation indications with a prespecified correlation indication comprises determining if each produced P-dimensional intensity correlation value is within a prespecified variation of intensity correlation values that is characteristic of historical process conditions for the plasma process, a produced intensity correlation value determined to not be within the prespecified variation of correlation values indicating a change in the status condition of the process.

19. The method of claim 18 wherein the step of determining if each produced P-dimensional intensity correlation value is within a prespecified variation of correlation values comprises, for a given intensity correlation value:

producing a measure of the difference between the given intensity correlation value and a mean of intensity correlation values characteristic of historical process conditions, and comparing the difference measure with a control limit that is prespecified for a maximum allowable variation of correlation values and generated based on historical process conditions.

20. The method of claim 19 wherein the step of determining if each produced P-dimensional intensity correlation value is within a prespecified variation of correlation values further comprises indicating a change in the status condition of the plasma process after a minimum number, c, of difference measures are compared with the prespecified control limit and found to indicate that the corresponding produced intensity correlation values are not within the prespecified correlation value variation.

21. The method of claim 19 further comprising:

a first step of carrying out a number, K, of historical plasma processes during each of which the intensity of a number, P, of a plurality of radiation wavelengths is monitored over a duration of time, T; and a second step of computing the mean, M(P), of the radiation wavelength intensity values for the P wavelengths over the time duration, T, for the K historical processes, and computing an inverse covariance, S, of a matrix of the radiation wavelength intensity values for the P wavelengths over the time duration, T, for the K historical processes;

and wherein the step of producing a measure of the difference between a given intensity correlation value and a mean of intensity correlation values comprises producing a difference measure given as:

$$T^2(t) = (D(P,t) - M(P)) * S * (D(P,t) - M(P))^T,$$

where t is the time during the plasma process to which the given intensity correlation value corresponds; D(P, t) is a matrix of the P radiation intensities monitored at time t; M(P) is the mean of the radiation wavelength intensity values for the P wavelengths over the time duration, T, for the K historical processes; S is the inverse covariance of the matrix of the radiation wavelength intensity values for the P wavelengths over the time duration, T, for the K historical processes; and the superscript T denotes transposition.

22. The method of claim 21 wherein the control limit is based on a confidence value and a distribution of the P radiation intensities monitored over the time duration, T, for the K historical processes.

23. The method of claim 22 wherein the control limit is based on a chi-squared distribution of the P radiation intensities monitored over the time duration, T, for the K historical processes.

24. The method of claim 1 wherein the step of producing indications of the P-dimensional intensity correlations comprises producing indications of maximum variations in correlations between the intensities of the P monitored radiation wavelengths during the plasma process as the plasma process proceeds, and wherein the step of comparing the produced correlation indications with a prespecified correlation indication comprises comparing the produced indications of maximum variations in correlations with prespecified maximum variation indications that are characteristic of historical process conditions, a produced indication of maximum correlation variation determined not to match a prespecified maximum variation indication representing a change in the status condition of the plasma process.

25. The method of claim 1 wherein the step of producing indications of the P-dimensional intensity correlations comprises producing indications of maximum variations in correlations between the intensities of the P monitored radiation wavelengths during the plasma process as the plasma process proceeds, and wherein the step of comparing the produced correlation indications wit h a prespecified correlation indication comprises comparing th e produced indications of maximum variations in correlations with prespecified maximum variation indications that are characteristic of historical process conditions, a produced indication of maximum ncorrelatio n variation determined to match a prespecified maximum variation indication representing a change in the status condition of the plasma process.

26. The method of claim 24 wherein the step of producing indications of maximum variations in correlations between the intensities of the P monitored radiation wavelengths comprises computing a number, S, of principal components of the variation in wavelength intensity correlation for the P radiation wavelengths monitored, each computed principal component corresponding to one of the P radiation wavelengths and each computed principal component being characterized by a computed eigenvalue magnitude, and wherein the step of comparing the produced indications of maximum variations in correlations with prespecified maximum variation indications that are characteristic of historical process conditions comprises comparing each of the number, S, of computed eigenvalue magnitudes with a corresponding prespecified eigenvalue magnitude that refers to a common one of the P radiation wavelengths.

27. The method of claim 24 wherein the step of producing indications of maximum variations in correlations between the intensities of the P monitored radiation wavelengths comprises computing a number, S, of principal components of the variation in wavelength intensity correlation for the P radiation wavelengths monitored, each computed principal component corresponding to one of the P radiation wavelengths and each computed principal component being characterized by a computed eigenvector orientation, and wherein the step of comparing the produced indications of maximum variations in correlations with prespecified maximum variation indications that are characteristic of historical process conditions comprises comparing each of the number, S, of computed eigenvector orientations with a corresponding prespecified eigenvector orientation that refers to a common one of the P radiation wavelengths.

28. The method of claim 27 further comprising the first steps of:
carrying out a number, K, of historical plasma processes during each of which the intensity of a number, P, of a plurality of radiation wavelengths is monitored over a duration of time, T;
computing a number, P, of historical principal components of the variation in wavelength intensity correlation for the P radiation wavelengths monitored over the time duration, T, for each of the K historical processes, each historical principal component being characterized by a historical orientation and a historical eigenvalue magnitude;
ranking the historical principal components for each of the K historical processes, in descending order based on historical eigenvalue magnitude;
retaining the first S historical principal components for each of the K historical processes based on a prespecified percentage in variation of intensity correlations that can be defined by the first S historical principal components for each of the K historical processes;
computing an average historical principal component for each of the S historical principal components across the K historical processes; and
computing an angle between each historical principal component eigenvector orientation and the eigenvector orientation of the corresponding computed average historical principal component; and
and wherein the step of comparing each of the number, S, of computed eigenvector orientations with a corresponding prespecified eigenvector orientation that refers to a common one of the P radiation wavelengths comprises comparing each of the number, S, of the computed eigenvector orientations with the historical eigenvector orientation of a corresponding one of the S computed average historical principal components.

29. The method of claim 28 further comprising a step of setting a prespecified threshold angle based on a prespecified percentage in variation of the computed historical eigenvector orientation angles for the K historical processes;
and further comprising the steps of:
computing an angle between each of the computed eigenvector orientations of the number, S, of the computed principal components and the historical eigenvector orientation of a corresponding one of the S computed average historical principal components; and
comparing each of the computed angles with the prespecified threshold angle, a computed angle determined to be less than the prespecified threshold angle indicating a change in the status condition of the plasma process.

30. The method of claim 1 wherein the step of producing indications of the P-dimensional intensity correlations comprises producing P-dimensional intensity correlation values, and wherein the step of comparing the produced correlation indications with a prespecified correlation indication comprises the steps of:
determining if each produced P-dimensional intensity correlation value is within a prespecified variation of intensity correlation values that is characteristic of historical process conditions for the plasma process;
for a produced intensity correlation value determined to not be within the prespecified variation of correlation values, producing indications of maximum variations in correlations between the intensities of the P monitored radiation wavelengths during the plasma process as the plasma process proceeds;
comparing the produced indications of maximum variations in correlations with prespecified maximum variation indications that are characteristic of historical process conditions, a produced indication of maximum correlation variation determined not to match a prespecified maximum variation indication representing a change in the status condition of the plasma process.

31. The method of claim 1 wherein the step of producing indications of the P-dimensional intensity correlations comprises producing P-dimensional intensity correlation values, and wherein the step of comparing the produced correlation indications with a prespecified correlation indication comprises the steps of:
determining if each produced P-dimensional intensity correlation value is within a prespecified variation of intensity correlation values that is characteristic of historical process conditions for the plasma process;
for a produced intensity correlation value determined to be within the prespecified variation of correlation values, producing indications of maximum variations in correlations between the intensities of the P monitored radiation wavelengths during the plasma process as the plasma process proceeds;
comparing the produced indications of maximum variations in correlations with prespecified maximum variation indications that are characteristic of historical process conditions, a produced indication of maximum correlation variation determined not to match a prespecified maximum variation indication representing a change in the status condition of the plasma process.

32. Apparatus for monitoring the status condition of a plasma process as the plasma process proceeds, comprising:
means for monitoring the intensity of each of a number, P, of a plurality of radiation wavelengths that are emitted from the plasma process as the process proceeds;
means for producing indications of P-dimensional correlations between the intensities of the P monitored wavelengths as the process proceeds; and
means for comparing the produced correlation indications with a prespecified correlation indication generated based on historical conditions for the plasma process, to determine the status condition of the process as the process proceeds.

33. The apparatus of claim 32 wherein the means for comparing comprises means for comparing the produced correlation indications with a prespecified correlation indication generated based on historical conditions for the plasma process, to determine if a condition of etch endpoint has been reached during a plasma etch process as the process proceeds.

34. The apparatus of claim 32 further comprising means for controlling parameters of the plasma process in response to process status condition determination.

35. The apparatus of claim 32 further comprising:

means for carrying out a number, K, of historical plasma processes during each of which the intensity of each of the P radiation wavelengths are monitored; and means for generating the prespecified correlation indication based on the intensities of the P monitored wavelengths for the process conditions of the K historical processes carried out.

36. The apparatus of claim 32 further comprising means for updating the prespecified correlation indication based on the produced correlation indication.

37. The apparatus of claim 32 further comprising:

means for monitoring the intensity of each of a number, J, of radiation wavelengths emitted from the plasma process as the process proceeds, where J>P; and means for filtering the J monitored wavelength intensities to select those P wavelengths that each meet a prespecified intensity criterion.

38. The apparatus of claim 32 wherein the means for monitoring the radiation wavelength intensities comprises means for monitoring the radiation wavelength intensities between about 200 nm and about 800 nm.

39. The apparatus of claim 32 wherein the means for producing indications of the P-dimensional intensity correlations comprises means for producing P-dimensional intensity correlation values, and wherein the means for comparing the produced correlation indications with a prespecified correlation indication comprises means for determining if each produced P-dimensional intensity correlation value is within a prespecified variation of intensity correlation values that is characteristic of historical process conditions for the plasma process, a produced intensity correlation value determined to not be within the prespecified variation of correlation values indicating a change in the status condition of the process.

40. The apparatus of claim 32 wherein the means for producing indications of the P-dimensional intensity correlations comprises means for producing indications of maximum variations in correlations between the intensities of the P monitored radiation wavelengths during the plasma process as the plasma process proceeds, and wherein the means for comparing the produced correlation indications with a prespecified correlation indication comprises means for comparing the produced indications of maximum variations in correlations with prespecified maximum variation indications that are characteristic of historical process conditions, a produced indication of maximum correlation variation determined not to match a prespecified maximum variation indication representing a change in the status condition of the plasma process.

* * * * *